(12) United States Patent
Hsu et al.

(10) Patent No.: US 11,512,072 B2
(45) Date of Patent: Nov. 29, 2022

(54) COMPOSITIONS AND METHODS FOR PREPARING AND USING AZETIDINES

(71) Applicant: University of Virginia Patent Foundation, Charlottesville, VA (US)

(72) Inventors: Ku-Lung Hsu, Charlottesville, VA (US); Rebecca L. McCloud, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 17/048,500

(22) PCT Filed: Apr. 19, 2019

(86) PCT No.: PCT/US2019/028340
§ 371 (c)(1),
(2) Date: Oct. 16, 2020

(87) PCT Pub. No.: WO2019/204740
PCT Pub. Date: Oct. 24, 2019

(65) Prior Publication Data
US 2021/0101884 A1    Apr. 8, 2021

Related U.S. Application Data

(60) Provisional application No. 62/659,892, filed on Apr. 19, 2018.

(51) Int. Cl.
| | |
|---|---|
| *C07D 403/04* | (2006.01) |
| *C07D 205/04* | (2006.01) |
| *C07D 205/12* | (2006.01) |
| *C07D 417/12* | (2006.01) |
| *C07D 413/04* | (2006.01) |
| *C07D 401/12* | (2006.01) |

(52) U.S. Cl.
CPC ......... *C07D 403/04* (2013.01); *C07D 205/04* (2013.01); *C07D 205/12* (2013.01); *C07D 401/12* (2013.01); *C07D 413/04* (2013.01); *C07D 417/12* (2013.01)

(58) Field of Classification Search
CPC .. C07D 403/04; C07D 205/04; C07D 205/12; C07D 417/12; C07D 413/04; C07D 401/12
See application file for complete search history.

(56) References Cited

U.S. PATENT DOCUMENTS

2015/0252034 A1* 9/2015 Pero ..................... C07D 413/14
514/210.21

FOREIGN PATENT DOCUMENTS

| WO | WO-2008036316 A2 | 3/2008 |
|---|---|---|
| WO | WO-2013063459 A1 | 5/2013 |
| WO | WO-2016101887 A1 | 6/2016 |
| WO | WO-2016164580 A1 | 10/2016 |
| WO | WO-2017215485 A1 | 12/2017 |
| WO | WO-2018102067 A2 | 6/2018 |
| WO | WO-2018149986 A1 | 8/2018 |
| WO | WO-2019204740 A1 | 10/2019 |

OTHER PUBLICATIONS

Chemical Abstracts Registry No. 1449201-23-3, indexed in the Registry file on STN CAS Online on Aug. 27, 2013. (Year: 2013).*
Chemical Abstracts Registry No. 1862926-73-5, indexed in the Registry file on STN CAS Online Feb. 9, 2016 (Year: 2016).*
Chemical Abstracts Registry No. 1465430-43-6, indexed in the Registry file on STN CAS Online Oct. 29, 2013. (Year: 2013).*
Chemical Abstracts Registry No. 1498454-34-4, indexed in the Registry file on STN CAS Online Dec. 19, 2013. (Year: 2013).*
Chemical Abstracts Registry No. 1849202-18-1, indexed in the Registry file on STN CAS Online Jan. 20, 2016. (Year: 2016).*
Chemical Abstracts Registry No. 1849218-79-6, indexed in the Registry file on STN CAS Online Jan. 20, 2016. (Year: 2016).*
Chemical Abstracts Registry No. 1877510-96-7, indexed in the Registry file on STN CAS Online Mar. 2, 2016. (Year: 2016).*
"Activity-Based Protein Profihng From Enzyme Chemistry to Proteomic Chemistry", Annual Review of Biochemistry, vol. 77 No. 1, (Mar. 26, 2008), 383-414.
"International Application Serial No. PCT/US2019/028340, International Search Report dated Aug. 9, 2019", 5 pgs.
"International Application Serial No. PCT/US2019/028340, Written Opinion dated Aug. 9, 2019", 7 pgs.
Max, Hansmann, et al., "Gold-allenylidenes an experimental and theoretical study Azetidines and Evaluation of Their Enhanced Thiol Reactivities", Chemical Science vol. 4, No. 4, (Jan. 1, 2013).
Palkowitz, Maximilian D., et al., "Synthesis of Diverse-Acryloyl Azetidines and Evaluation of Their Enhanced Thiol Reactivities", Organic Letters, vol. 19 No. 9, (Apr. 20, 2017), 2270-2273.
"International Application Serial No. PCT/US2019/028340, International Preliminary Report on Patentability dated Oct. 29, 2020", 9 pgs.

* cited by examiner

*Primary Examiner* — Laura L Stockton
(74) *Attorney, Agent, or Firm* — Schwegman Lundberg & Woessner, P.A.

(57) ABSTRACT

The present disclosure provides azetidine compounds of Formula I and their pharmaceutically acceptable salts, their compositions, and methods for their use in determining azetidine compound binding to proteins. The azetidine compounds are useful as probes, for monitoring diacylglycerol kinase activity, and for identifying druggable targets.

5 Claims, 5 Drawing Sheets

FIG. 5

| Protein | Peptide | Modified Site | Persulfide |
|---|---|---|---|
| GSTP1 | ASCLYGQLPK | C47 | Yes |
| RL24 | CEASAFLSK | C35 | NO |
| SAE2 | VLVVGAGGIGCELLK | C29 | NO |
| SERA | NAGNCLSPAVIVGLLK | C369 | NO |
| GAPDH | IISNASCTTNCLAPLAK | C152 | YES |
| HS90B | VFMIDSCDELIPEYNFIR | C365 | YES |
| PEBP1 | APVAGTCYQAEWDDYVPK | C167 | YES |
| RL23 | ISLGLPVGAVINCADNTGAK | C27 | YES |
| RPGF2 | VDDCQFVCIAQQDYCR | C224 | NO |
| RS16 | TATAVAHCK | C24 | NO |
| RS5 | VNQAIWLLCTGAR | C154 | NO |
| RS11 | CPFTGNVSIR | C58 | NO |
| RS3 | GLCAIAQAESLR | C96 | YES |
| RS4X | FDTGNLCMVTGGANLGR | C180 | YES |
| DGK alpha | VLVSGQECK | C342 | ? |
| | TTDVTSLCTPEAFR | C353 | ? |
| | VLVCGGDGTVGWLETIDK | C423 | ? |
| | DGSGCVSLAEWVR | C171 | ? |

COMPOSITIONS AND METHODS FOR PREPARING AND USING AZETIDINES

This application is a U.S. National Stage filing under 35 U.S.C. § 371 of PCT Patent Application No. PCT/US2019/028340, filed on Apr. 19, 2019, which claims the benefit of priority to U.S. Provisional Patent Application No. 62/659,892, filed on Apr. 19, 2018, which applications are incorporated by reference as if fully set forth herein.

STATEMENT OF GOVERNMENT SUPPORT

This invention was made with government support under grant No. 2018255830 awarded by the National Science Foundation. The U.S. government has certain rights in the invention.

BACKGROUND

Azetidine is a saturated heterocyclic organic compound containing three carbon atoms and one nitrogen atom. It is a liquid at room temperature with a strong odor of ammonia and is strongly basic compared to most secondary amines. Azetidines do not occur as frequently in nature and have been studied far less than closely related chemical compounds such as pyrrolidine and β-lactam. Azetidine and its derivatives are relatively rare structural motifs in natural products. Notably, they are a key component of mugineic acids and penaresidins. Perhaps the most abundant azetidine containing natural product is azetidine-2-carboxylic acid, a non-proteinogenic homolog of proline.

For improving bioavailability, preventing metabolic degradation, or to add compact functional groups, a significant majority of approved drugs will contain a nitrogen heterocycle[1, 2]. Piperidines and piperazines still remain the most common heterocycles, while other heterocycles have been largely unexplored. For example, azetidines, four-membered nitrogen heterocycles, are relatively rare in approved drugs. Azetidines possess many desirable properties, such as enhanced solubility, metabolic stability, and 3-D characteristics that could be used to enhance target engagement for inhibitors, yet they have just begun to appear in drug-like molecules. More recently, azetidines have been used to enhance the rate of thiol reactions with acrylamides[3], incorporated into antimalarial inhibitors (BRD7929, BRD391.4) targeting the parasitic tRNA-synthase[4, 5], and appear in the hypertension drug Azelnidipine[6, 7].

SUMMARY OF THE PRESENT DISCLOSURE

The present disclosure addresses these and other needs by providing, in some embodiments, activity-based probes (ABPs) containing azetidine scaffolds as new chemical entities to target druggable binding pockets of proteins, such as human proteins. Without wishing to be bound by any particular theory, it is hypothesized herein that azetidines can be prepared as novel chemical probes useful for academic discovery and for development of drug leads for indications in immunology, cancer, inflammation, and metabolic disease.

Other useful azetidines and their preparation can be found in the Examples and in the Appendices.

In one embodiment, the present application discloses compositions and methods for tailoring azetidine reactivity. In another embodiment, an azetidine of the present disclosure is useful as a probe and is useful for monitoring diacylglycerol kinase activity and for targeting proteins. In still another embodiment, the diacylglycerol kinase activity is DGKα activity.

The present disclosure provides, in various embodiments, azetidine compounds of Formula I and their pharmaceutically acceptable salts:

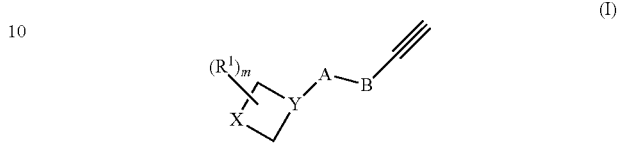

(I)

In Formula I compounds, A is —NH—, —C(O)—, or —CH$_2$—. When A is —C(O)— or —CH$_2$—, then X is CR$^2$R$^3$ and Y is N. When A is —NH—, then X is NR$^4$ and Y is CH.

B is a divalent linking group that is a bond, C$_1$-C$_6$-alkylene, or —(C$_1$-C$_6$-alkylene)(C$_6$-C$_{12}$-arylene).

R$^1$ is selected from the group consisting of H, C$_6$-C$_{12}$-aryl.

R$^2$ and R$^3$ are independently selected from the group consisting of H, C$_1$-C$_6$-alkyl, —NRR' (wherein R and R' are independently selected from H and C$_1$-C$_6$ alkyl), —(C$_1$-C$_6$-alkyl)(C$_6$-C$_{12}$-aryl) (wherein the alkyl is optionally interrupted by one or more —O—); C$_6$-C$_{12}$-aryl; —O—(C$_6$-C$_{12}$-aryl); 5- to 12-membered heteroaryl (wherein one or more members is selected from N, O, and S), 5- to 12-membered —O-(heteroaryl) (wherein one or more members is selected from N, O, and S). When B is C$_1$-C$_6$-alkylene, then at least one of R$^2$ and R$^3$ is selected from —(C$_1$-C$_6$-alkyl)(C$_6$-C$_{12}$-aryl), C$_6$-C$_{12}$-aryl, —O—(C$_6$-C$_{12}$-aryl), 5- to 12-membered heteroaryl except triazole and diazole, and 5- to 12-membered —O-(heteroaryl) as defined above.

In some embodiments, R$^2$ and R$^3$ in combination with the ring carbon atom to which they are bound form a spiro-fused C$_3$-C$_8$-cycloalkyl.

R$^4$ is selected from the group consisting of C$_6$-C$_{12}$-alyl, 5- to 12-membered heteroaryl (wherein one or more members is selected from N, O, and S), 5- to 12-membered —O-(heteroaryl) (wherein one or more members is selected from N, O, and S), and 4- to 12-membered heterocycle (wherein one or more members is selected from N, O, and S).

Subscript m is 0, 1, 3, or 4.

In Formula I, any aryl, heterocycle, or heteroaryl is optionally substituted with one to four substituents selected from the group consisting of halogen, hydroxy, cyano, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, and carboxy.

In additional embodiments, the present disclosure provides a method for determining the binding of an azetidine compound to a protein. The method comprises (A) contacting an azetidine compound as described herein with a test sample comprising at least one protein to yield a first product; (B) contacting the first product with an azide-tag reagent in a copper-catalyzed azide-alkyne cycloaddition reaction to yield a second product; and (C) detecting the formation of any tag-modified proteins in the second product.

In an embodiment, the present disclosure provides new and useful azetidines as described herein and methods for analyzing and measuring their activity.

In an embodiment, azetidines of the present disclosure are attached or linked to other molecules as drugs or to be used to discover protein targets.

The present disclosure further provides kits. Kits of the present disclosure comprise at least one compound of the present disclosure and an instructional material for the use thereof, and optionally an applicator.

BRIEF DESCRIPTION OF THE DRAWINGS

FIG. 5. Azetidine compound TH071 binds to cysteine residues, roughly half of which play a role in forming sulfhydration bonds on proteins.

DETAILED DESCRIPTION

Definitions

Figure 1:
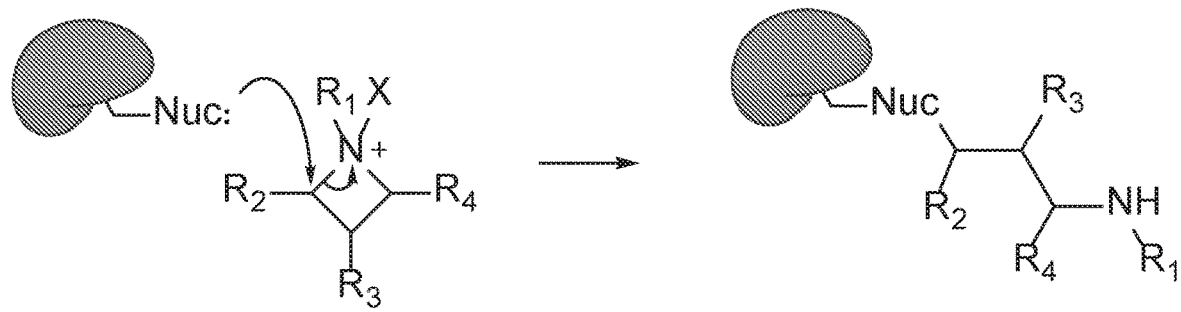
FIG. 1. Formation of covalent bonds between a nucleophile protein and representative azetidine compound (substituent labeling is arbitrary).

In describing and claiming the present disclosure, the following terminology will be used in accordance with the definitions set forth below. Unless defined otherwise, all technical and scientific terms used herein have the commonly understood by one of ordinary skill in the art to which the present disclosure pertains. Although any methods and materials similar or equivalent to those described herein may be useful in the practice or testing of the present disclosure, preferred methods and materials are described below. Specific terminology of particular importance to the description of the present disclosure is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present disclosure, refers to the use or administration of a compound for an additional therapeutic use for a particular injury, disease, or disorder being treated. Such a compound, for example, could include one being used to treat an unrelated disease or disorder, or a disease or disorder, which may not be responsive to the primary treatment for the injury, disease or disorder being treated.

As use herein, the terms "administration of" and or "administering" a compound should be understood to mean providing a compound of the present disclosure or a prodrug of a compound of the present disclosure to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, an "analog", or "analogue" of a chemical compound is a compound that, by way of example, resembles another in structure but is not necessarily an isomer e.g., 5-fluorouracil is an analog of thymine).

An "antagonist" is a composition of matter that when administered to a mammal such as a human, inhibits a biological activity attributable to the level or presence of a compound or molecule of interest in the subject.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

The term "biological sample," as used herein, refers to samples obtained from a subject, including, but not limited to, skin, hair, tissue, blood, plasma, serum, cells, sweat, saliva, feces, tissue and/or urine.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "compound," as used herein, refers to any type of substance or agent that is commonly considered a drug, or a candidate for use as a drug, as well as combinations and mixtures of the above. When referring to a compound of the present disclosure, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The terms "comprises", "comprising", and the like can have the meaning ascribed to them in U.S. Patent Law and can mean "includes", "including" and the like. As used herein, "including" or "includes" or the like means including, without limitation.

The term "delivery vehicle" refers to any kind of device or material that can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example," "for instance," "such as," "including" and the like are meant to introduce examples that further clarify more general subject matter. Unless otherwise specified, these examples are provided only as an aid for understanding the present disclosure, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

As used herein, "homology" is used synonymously with "identity."

The term "inhibit," as used herein, refers to the ability of a compound of the present disclosure to reduce or impede a described function, such as having inhibitory sodium channel activity. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

As used herein "injecting or applying" includes administration of a compound of the present disclosure by any number of routes and means including, but not limited to, topical, oral, buccal, intravenous, intramuscular, intraarterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression, which can be used to communicate the usefulness of the peptide of the present disclosure in the kit for effecting alleviation of the various diseases or disorders recited herein. Optionally, or alternately, the instructional material may describe one or more methods of alleviating the diseases or disorders in a cell or a tissue of a mammal. The instructional material of the kit of the present disclosure may, for example, be affixed to a container that contains the identified compound present disclosure or be shipped together with a container that contains the identified compound. Alternatively, the instructional material may be shipped separately from the container with the intention that the instructional material and the compound be used cooperatively by the recipient.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "modulate", as used herein, refers to changing the level of an activity, function, or process. The term "modulate" encompasses both inhibiting and stimulating an activity, function, or process.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker. Standard can also refer to a healthy individual.

A "subject" is a vertebrate, including a mammal, such as a human. Mammals include, but are not limited to, humans, farm animals, sport animals, and pets.

A "subject in need thereof" is a patient, animal, mammal, or human, who will benefit from the method of this present disclosure—for example, one who is at risk of inflammation or who has inflammation, has been infected with a pathogen, exposed to an allergen, been injured, etc. Furthermore, based on the teachings of the present disclosure a clinician or other professional can determine if a preventive treatment may be necessary.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound that is sufficient to provide a beneficial effect to the subject to which the compound is administered.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

A "$C_1$-$C_n$ alkylene" is a divalent moiety that otherwise has the same meaning as "$C_1$-$C_n$ alkyl" as defined herein.

The term "$C_2$-$C_n$ alkenyl" wherein n is an integer, as used herein, represents an unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated brandied or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_1$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g. from 1 to 4 times) with independently selected halogen, hydroxy, cyano, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

As used herein the term "aryl" refers to a optionally substituted mono- or bicyclic $C_6$-$C_{12}$ carbocyclic ring system having one or two aromatic rings including, but not limited to, phenyl, benzyl, naphthyl, tetrahydronaphthyl, indanyl, indenyl, and the like. Optionally substituted aryl includes aryl compounds having from zero to four substituents, and substituted aryl includes aryl compounds having one or more substituents. To illustrate, the term ($C_5$-$C_8$ alkyl)aryl refers to any aryl group that is attached to the parent moiety via the alkyl group.

An "arylene" is a divalent moiety that otherwise has the same definition of "aryl" as defined herein.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and that consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and that consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e. S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7-to 12-membered bridged or fused bicyclic carbon ring. The bicyclic ring may be attached at any carbon atom that affords a stable structure. The term includes, but is not limited to, naphthyl, dicyclohexyl, dicyclohexenyl, and the like.

The compounds of the present disclosure contain one or more asymmetric centers in the molecule. In accordance with the present disclosure a structure that does not designate the stereochemistry is to be understood as embracing all the various optical isomers, as well as racemic mixtures thereof.

The compounds of the present disclosure may exist in tautomeric forms and the present disclosure includes both mixtures and separate individual tautomers. For example, the following structure:

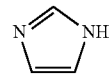

is understood to represent a mixture of the structures:

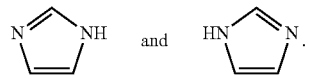 [SMILES: c1c[nH]cn1 ; c1c[nH]cn1]

The term "pharmaceutically acceptable salt" refers to salts that retain the biological effectiveness and properties of the compounds of the present disclosure and that are not biologically or otherwise undesirable. In many cases, the compounds of the present disclosure are capable of forming acid and/or base salts by virtue of the presence of amino and/or carboxyl groups or groups similar thereto. Further, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

Compounds of the present disclosure that have one or more asymmetric carbon atoms may exist as the optically pure enantiomers, or optically pure diastereomers, as well as mixtures of enantiomers, mixtures of diastereomers, and racemic mixtures of such stereoisomers. The present disclosure includes within its scope all such isomers and mixtures thereof.

Compounds

The compounds of the present disclosure are useful, in some embodiments, as activity-based probes (ABPs) for elucidating biological targets of azetidine-based therapeutics. Activity-based protein profiling (ABPP) is a method utilizing chemical probes to study proteins in their native context. Using ABPs, proteins are targeted and labeled based on their mechanism of actions. Most probes consist of an electrophile, or 'warhead', and a reporter tag. Warhead reactive groups form covalent bonds with proteins, generally through acyl substitutions or 1-2 additions[8]. After the probe is bound, the reporter tag is used to visualize proteins either by SDS-PAGE fluorescence scanning or for affinity enrichment for liquid chromatography tandem mass spectrometry (LC-MS/MS) analysis. ABPP has allowed for the elucidation of protein function, post-translational modifications, and enabled screening for selective pharmacological agents in academic and clinical endeavors[9, 10].

Compounds of the present disclosure all contain azetidine rings that are considered to be stable, but they do possess a significant amount of ring strain. As a result of their inherent stability, azetidine ring-opening reactions require both a strong Lewis acid and nucleophile[11-15]. In many instances, alcohol and thiol nucleophiles are employed to achieve ring-opening[12], and these nucleophiles bear resemblance to amino acids such as serine or cysteine. This observation suggested that either through metal-binding or protonation by nearby acidic residues, azetidines are capable of being activated to form an azetidinium ions. The ring strain in azetidines drives the reaction forward, resulting in formation of irreversible covalent bonds between the azetidine and the target protein (FIG. 1). In addition to developing chemical probes with novel mechanisms, we disclose the biological activity of azetidine compounds and their use for inhibitor development.

Thus, in various embodiments, the present disclosure provides azetidine compounds of Formula I and their pharmaceutically acceptable salts:

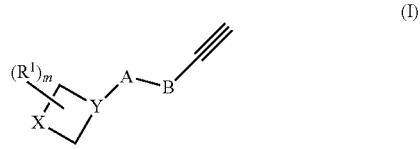

(I)

In Formula I compounds, A is —NH—, —C(O)—, or —CH$_2$—. When A is —C(O)— or —CH$_2$—, then X is CR$^2$R$^3$ and Y is N. When A is —NH—, then X is NR$^4$ and Y is CH.

B is a divalent linking group that is a bond, C$_1$-C$_6$-alkylene, or —(C$_1$-C$_6$-alkylene)(C$_6$-C$_{12}$-arylene).

R$^1$ is selected from the group consisting of H, C$_6$-C$_{12}$-aryl.

R$^2$ and R$^3$ are independently selected from the group consisting of H, C$_1$-C$_6$-alkyl, —NRR' (wherein R and R' are independently selected from H and C$_1$-C$_6$-alkyl), —(C$_1$-C$_6$-alkyl)(C$_6$-C$_{12}$-aryl) (wherein the alkyl is optionally interrupted by one or more —O—); C$_6$-C$_{12}$-aryl; —O—(C$_6$-C$_{12}$-aryl); 5- to 12-membered heteroaryl (wherein one or more members is selected from N, O, and S), 5- to 12-membered —O-(heteroaryl) (wherein one or more members is selected from N, O, and S). When B is C$_1$-C$_6$-alkylene, then at least one of R$^2$ and R$^3$ is selected from —(C$_1$-C$_6$-alkyl)(C$_6$-C$_{12}$-aryl), C$_6$-C$_{12}$-aryl, —O—(C$_6$-C$_{12}$-aryl), 5- to 12-membered heteroaryl except triazole and diazole, and 5- to 12-membered —O-(heteroaryl) as defined above.

In some embodiments, R$^2$ and R$^3$ in combination with the ring carbon atom to which they are bound form a spiro-fused C$_3$-C$_8$-cycloalkyl.

R$^4$ is selected from the group consisting of C$_6$-C$_{12}$-amyl, 5- to 12-membered heteroaryl (wherein one or more members is selected from N, O, and S), 5- to 12-membered —O-(heteroaryl) (wherein one or more members is selected from N, O, and S), and 4- to 12-membered heterocycle (wherein one or more members is selected from N, O, and S).

Subscript m is 0, 1, 2, 3, or 4.

In Formula I, any aryl, heterocycle, or heteroaryl is optionally substituted with one to four substituents selected from the group consisting of halogen, hydroxy, cyano, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, and carboxy.

In some embodiments, A is —C(O)— or —CH$_2$—; X is CR$^2$R$^3$; and Y is N. In other embodiments, A is —CH$_2$—.

Pursuant to yet other embodiments, m is 0 or 1. Optionally in combination with this or any other embodiment herein described, R$^1$ is phenyl.

In an embodiment, R$^2$ and R$^3$ are independently selected from the group consisting of H, C$_1$-C$_6$-alkyl, 5- to 12-membered heteroaryl (wherein one or more members is selected from N, O, and S), and 5- to 12-membered —O-(heteroaryl) (wherein one or more members is selected from N, O, and S).

In another embodiment, optionally in combination with any other embodiment, R$^2$ is H.

Some Formula I compounds, in accordance with various embodiments, are those in which A is —NH—; X is NR$^4$, and Y is CH. In exemplary compounds, per some embodiments, R$^4$ is C$_6$-C$_{12}$-aryl or 5- to 12-membered heteroaryl (wherein one or more members is selected from N, O, and S).

Still further embodiments provide for a Formula I compound wherein A is —CH$_2$—; X is CR$^2$R$^3$; Y is N; B is —CH$_2$CH$_2$—; and R$^2$ is H.

Specific examples of Formula I compounds or pharmaceutically acceptable salts thereof include those illustrated in the table below:

| Example | Structure |
| --- | --- |
| TH055 | 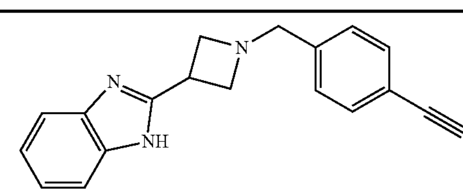 |
| TH056 | 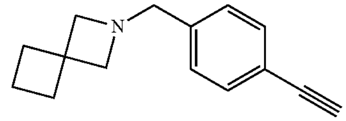 [SMILES: C#Cc1ccc(CN2CC3(CCC3)C2)cc1] |
| TH057 | 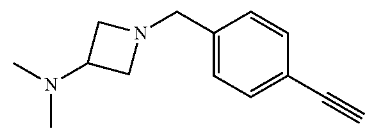 [SMILES: C#Cc1ccc(CN2CC(N(C)C)C2)cc1] |

-continued
| Example | Structure |
|---|---|
| RLM-1451 | 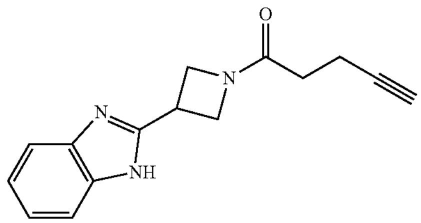 [SMILES: C#CCCC(=O)N1CC(c2nc3ccccc3[nH]2)C1] |
| RLM-1452 | 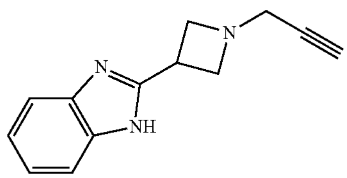 [SMILES: C#CCN1CC(c2nc3ccccc3[nH]2)C1] |
| RLM-1453 | 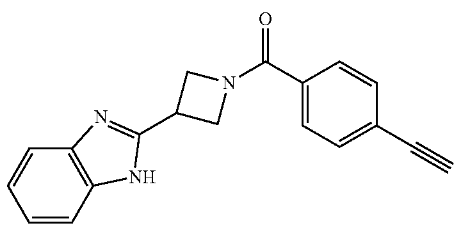 [SMILES: C#Cc1ccc(C(=O)N2CC(c3nc4ccccc4[nH]3)C2)cc1] |
| RLM-207 | 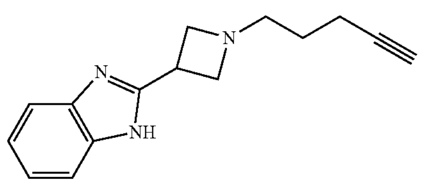 [SMILES: C#CCCCN1CC(c2nc3ccccc3[nH]2)C1] |
| RLM-266 | 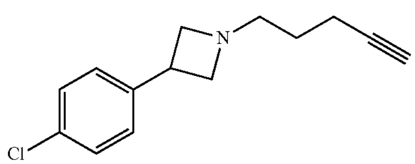 [SMILES: C#CCCCN1CC(c2ccc(Cl)cc2)C1] |
| RLM-275 | 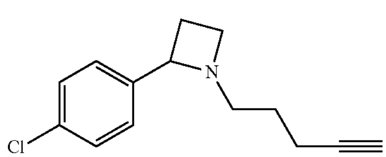 [SMILES: C#CCCCN1CCC1c1ccc(Cl)cc1] |
| RLM-277 | 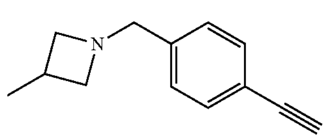 |
| TH058 | 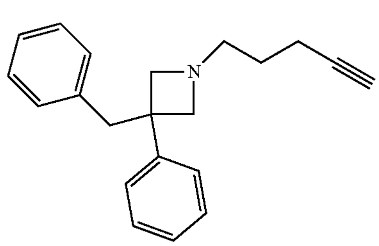 [SMILES: C#CCCCN1CC(Cc2ccccc2)(c2ccccc2)C1] |
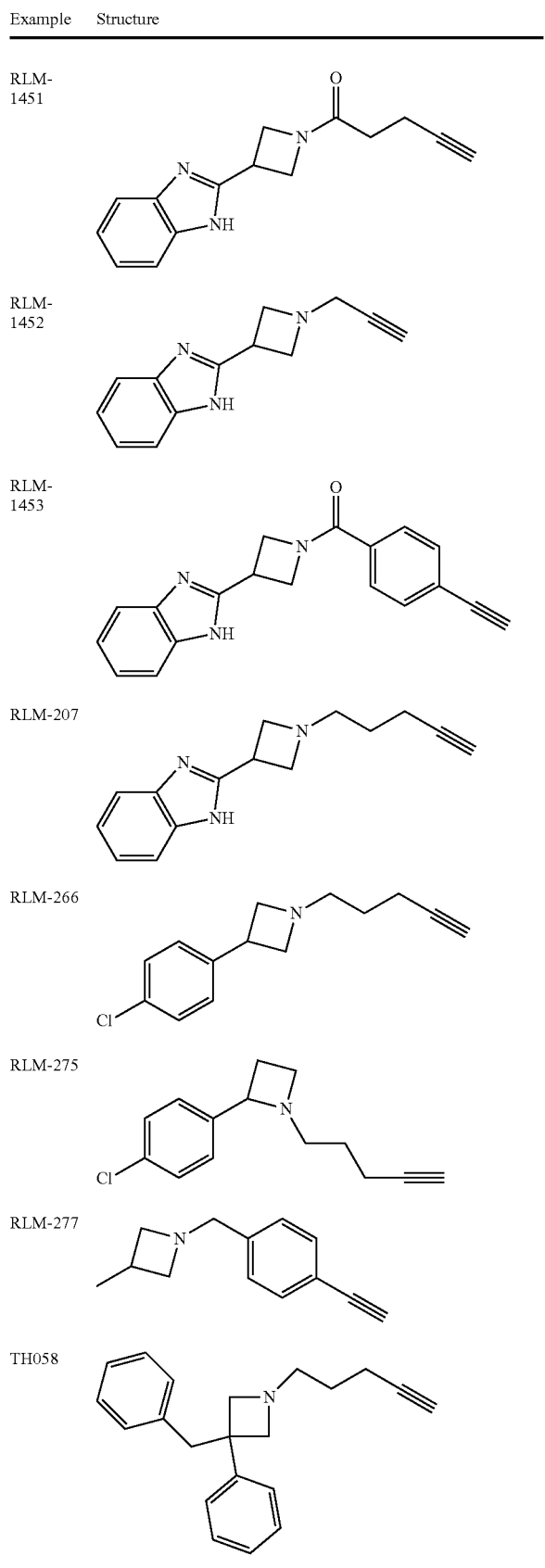
-continued
| Example | Structure |
|---|---|
| TH059 | 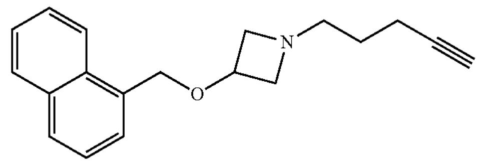 [SMILES: C#CCCCN1CC(OCc2cccc3ccccc23)C1] |
| TH060 | 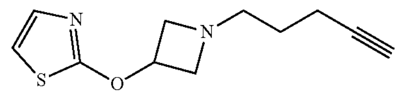 |
| TH061 | 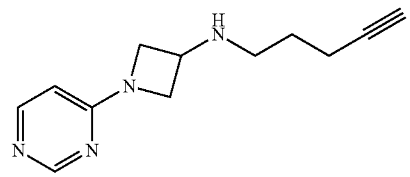 [SMILES: C#CCCCNC1CN(c2ccncn2)C1] |
| TH062 | 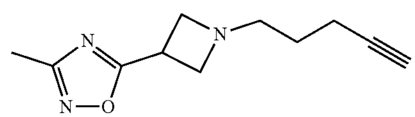 |
| TH064 | 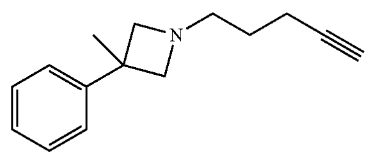 [SMILES: C#CCCCN1CC(C)(c2ccccc2)C1] |
| TH065 | 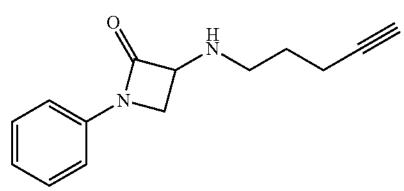 [SMILES: C#CCCCNC1CN(c2ccccc2)C1=O] |
| TH066 | 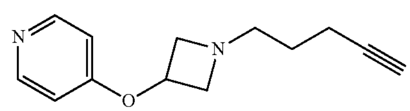 [SMILES: C#CCCCN1CC(Oc2ccncc2)C1] |
| TH067 | 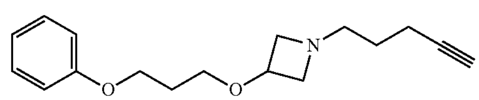 [SMILES: C#CCCCN1CC(OCCCOc2ccccc2)C1] |
| TH068 | 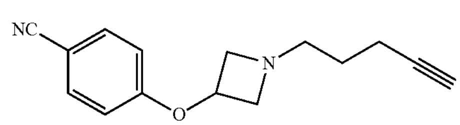 [SMILES: C#CCCCN1CC(Oc2ccc(C#N)cc2)C1] |
| TH069 | 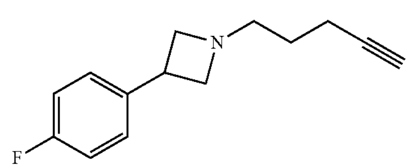 [SMILES: C#CCCCN1CC(c2ccc(F)cc2)C1] |
| TH070 | 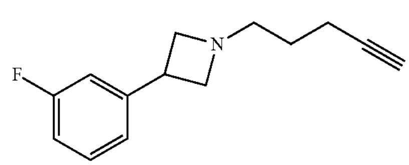 [SMILES: C#CCCCN1CC(c2cccc(F)c2)C1] |
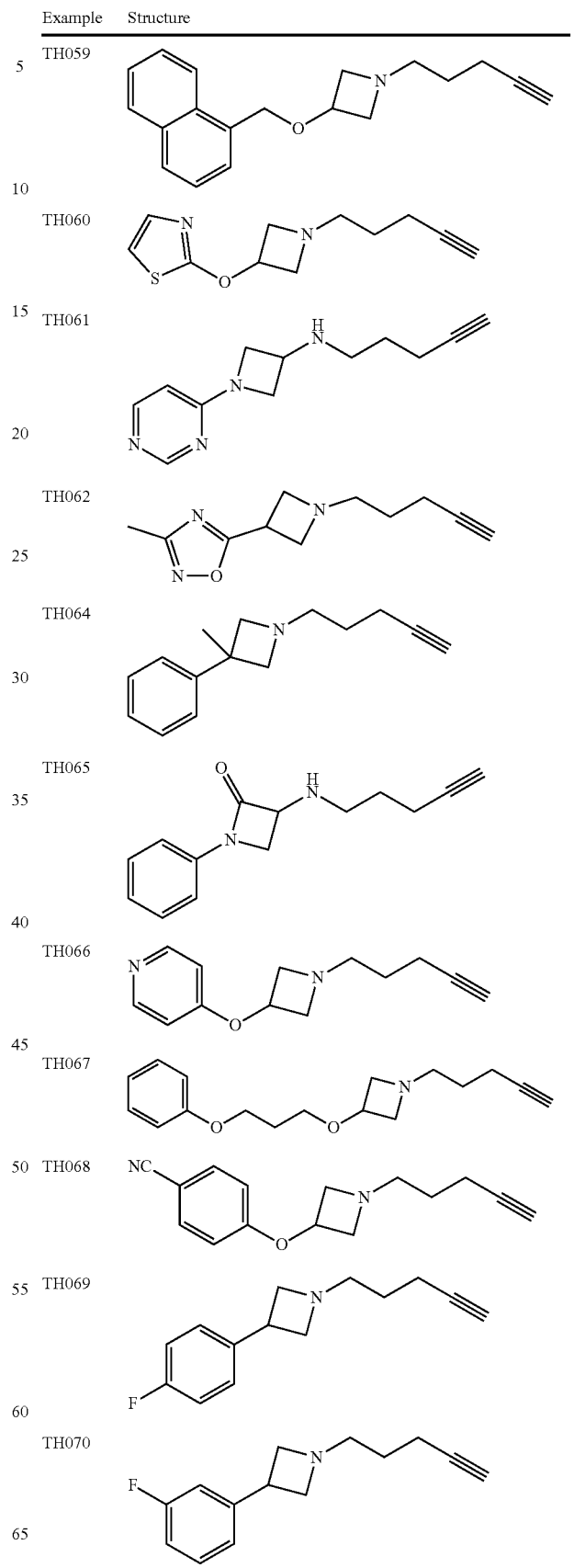

| Example | Structure |
|---|---|
| TH071 | 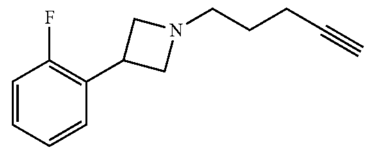 [SMILES: C#CCCCN1CC(c2ccccc2F)C1] |
| TH072 | 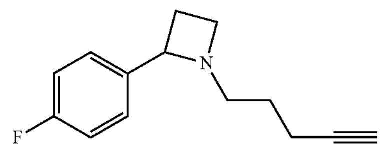 [SMILES: C#CCCCN1CCC1c1ccc(F)cc1] |
| TH073 | 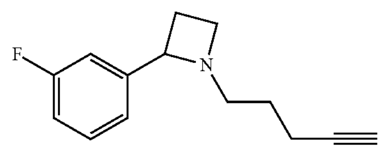 |
| TH074 | 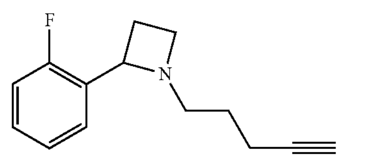 [SMILES: C#CCCCN1CCC1c1ccccc1F] |

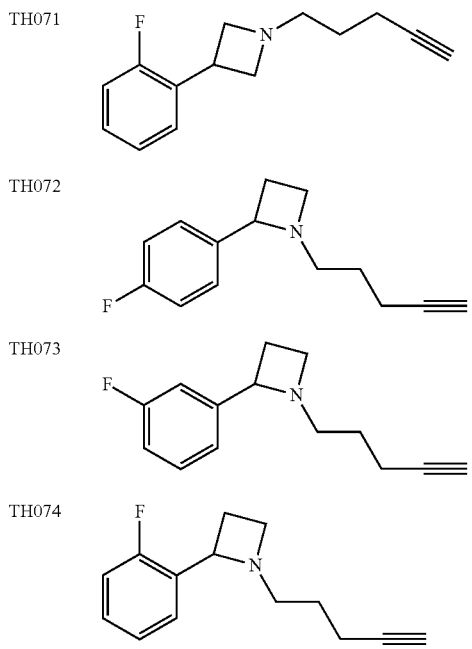

Methods

One advantage of the azetidine compounds of the present disclosure is their ability to bind proteins in their native contexts, such as in active conformations. Another advantage is that the azetidine compounds are useful in identifying biological targets in their native environments, i.e. in situ, such as in live cells. As the data herein shows, the azetidine compounds of the present disclosure are amenable to structural tuning. Because the azetidine compounds exhibit different reactivities toward proteins, they are useful for identifying various druggable targets.

The present disclosure thus provides in an embodiment a method for determining the binding of an azetidine compound as described herein to a protein. The method comprises (A) contacting an azetidine compound according to any one of claims 1 to 11 with a test sample comprising at least one protein to yield a first product; (B) contacting the first product with an azide-tag reagent in a copper-catalyzed azide-alkyne cycloaddition reaction to yield a second product; and (C) detecting the formation of any tag-modified proteins in the second product.

In some embodiments, the detection of a tag-modified protein in the second product correlates to a determination that the azetidine compound binds to the protein. The detecting is achieved by any of a variety of standard methodologies known in the art, such as a gel assay as exemplified herein.

In one embodiment, the method is useful for determining the binding of an azetidine compound to a test sample containing just a single protein of interest. In another embodiment, the test sample comprises a plurality of different proteins, such as in live cells and cell lysates. A useful test sample is the human proteome.

The method is not limited to any particular azide-tag reagent. In general, the azide-tag reagent is one amenable to use in CLICK chemistry, such as commercially available CLICK-able fluorescent dyes that allow subsequent visualization by fluorescence spectroscopy. Thus, in some embodiments, the azide-tag reagent comprises a fluorophore tag, such as in rhodamine azide. In other embodiments, the azide-tag reagent contains a tag that is selected from a variety of known affinity probes, such as biotin and desthiobiotin.

In various embodiments, the method further comprises the step of identifying the azetidine compound binding site or sites on the tagged proteins. Methodologies that are routine in the art are useful for carrying out the identification. An exemplary protein analysis entails trypsin digestion of the tagged proteins, and subjecting the resulting peptides to liquid chromatography and mass spectrometry to obtain protein sequence data, thereby identifying what sites on the protein were tagged.

In some embodiments, one or more proteins in step A is isotopically labeled for use in differential proteomics, for example. Useful isotopes include $^{13}C$, $^{15}N$, $^{2}H$ (deuterium), and $^{18}O$. Well known methodologies in the art can be employed for obtaining isotopically labeled proteins from commercially available isotope-labeled amino acids, such as cell-based and cell-free labeling techniques.

The following non-limiting examples illustrate and provide additional embodiments of the present disclosure.

EXAMPLES

Synthesis of Azetidine Activity-Based Probes

Azetidines were ordered from a commercial source and modified with alkyne substituents to yield compounds of Formula I as illustrated by general synthetic routes shown in Schemes 1 and 2 below.

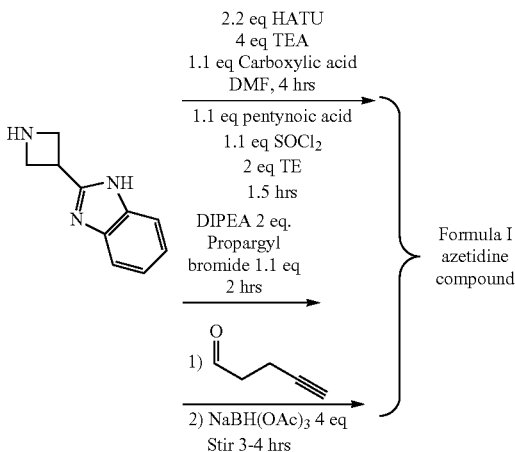

Scheme 1

Scheme 2

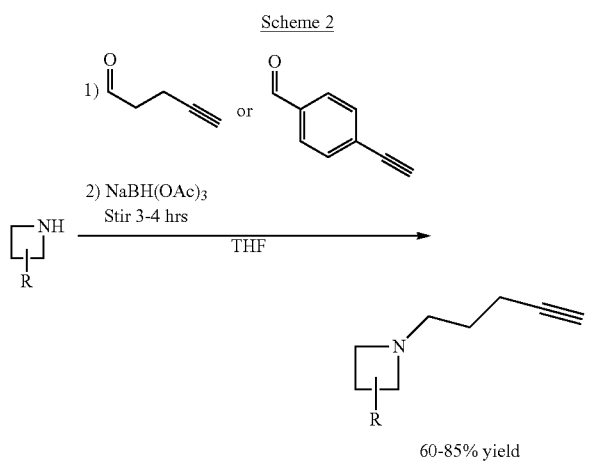

60-85% yield

Reductive aminations, as shown specifically in Scheme 2, were conducted in tetrahydrofuran, combining the aldehyde and azetidine at a 1.1:1 molar ratio, respectively, optionally in the presence of 1 mol eq. of triethylamine (TEA) to facilitate the reaction. Formation of imine intermediates was confirmed by TLC before adding 4 eq. of NaBH(OAc)$_3$. Formation of final product was confirmed by TLC, usually occurring to completion within 4 hrs. The reaction mixture was diluted with dichloromethane, and the organic layer was washed three times with sodium bicarbonate. The organic layer was dried with MgSO$_4$, filtered, concentrated, and purified via preparative TLC. Azetidine compound products were identified via mass spectrometry, and proton and carbon NMR.

Table 1 below presents characterizing data for exemplary compounds that were synthesized by the general procedures described above.

TABLE 1

| Example | Structure | $^1$H-NMR |
|---|---|---|
| TH055 | 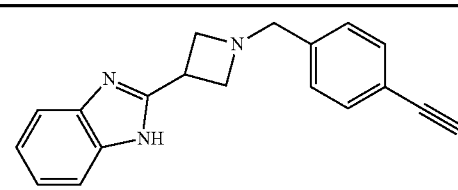 | $^1$H NMR (600 MHz, Chloroform-d) δ 7.55 (s, 2H), 7.45-7.38 (m, 2H), 7.21 (dt, J = 7.1, 2.6 Hz, 4H), 3.82 (s, 1H), 3.69-3.55 (m, 4H), 3.51 (s, 2H), 3.05 (s, 1H). |
| TH056 | 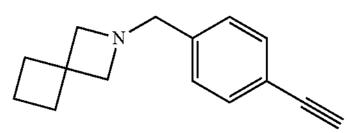 [SMILES: C#Cc1ccc(CN2CC3(CCC3)C2)cc1] | $^1$H NMR (600 MHz, Chloroform-d) δ 7.43 (d, J = 7.6 Hz, 2H), 7.25 (s, 2H), 3.65 (s, 2H), 3.32 (s, 4H), 3.05 (s, 1H), 2.11 (t, J = 7.7 Hz, 4H), 1.78 (p, J = 7.6 Hz, 2H). |
| TH057 | 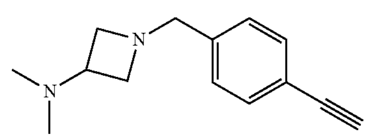 [SMILES: C#Cc1ccc(CN2CC(N(C)C)C2)cc1] | $^1$H NMR (600 MHz, Chloroform-d) δ 7.42 (d, J = 8.0 Hz, 2H), 7.22 (d, J = 7.9 Hz, 2H), 3.61 (s, 2H), 3.49 (q, J = 4.6, 3.4 Hz, 2H), 3.03 (s, 1H), 2.88 (d, J = 4.3 Hz, 3H), 2.09 (d, J = 0.7 Hz, 6H). |
| RLM-1451 | 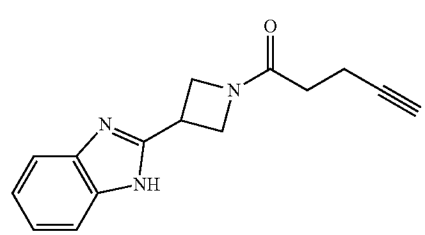 [SMILES: C#CCCC(=O)N1CC(c2nc3ccccc3[nH]2)C1] | 1H NMR (600 MHz, Chloroform-d) δ 7.56 (broad s, 2H), 7.22 (dt, J = 6.00 Hz, 2H), 4.60 (dd, J = 8.5, 5.8 Hz, 1H), 4.55 (t, J = 8.6 Hz, 1H), 4.36 (t, J = 6.9 Hz, 2H), 4.12 (t, J = 7.5 Hz, 1H), 2.46 (dddd, J = 23.9, 17.0, 9.6, 2.5 Hz, 2H), 2.32 (dt, J = 14.8, 7.3 Hz, 1H), 2.23 (dt, J = 15.1, 7.1 Hz, 1H), 1.95 (t, J = 2.6 Hz, 1H) |

TABLE 1-continued

| Example | Structure | ¹H-NMR |
|---|---|---|
| RLM-1452 | 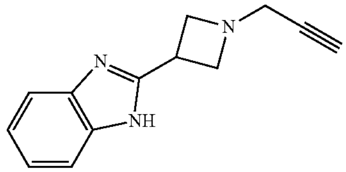 [SMILES: C#CCN1CC(c2nc3ccccc3[nH]2)C1] | 1H NMR (600 MHz, Chloroform-d) δ 7.56 (broad s, 2H), 7.23 (m, 2H), 3.78 (d, J = 3.0 Hz, 3H), 3.52 (d, J = 3.3 Hz, 2H), 3.36 (d, J = 2.4 Hz, 2H), 2.31 (t, J = 2.4 Hz, 1H) |
| RLM-1453 | 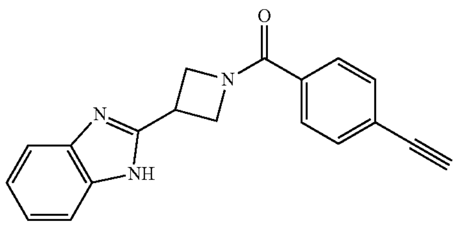 [SMILES: C#Cc1ccc(C(=O)N2CC(c3nc4ccccc4[nH]3)C2)cc1] | 1H NMR (600 MHz, Chloroform-d) δ 7.51 (broad s, 2H), 7.46-7.38 (m, 4H), 7.21 (m, 2H), 4.77 (d, J = 15.4 Hz, 1H), 4.55 (ddd, J = 42.2, 20.2, 8.0 Hz 3H), 4.15 (m, 1H), 3.18 (s, 1H) |
| RLM-207 | 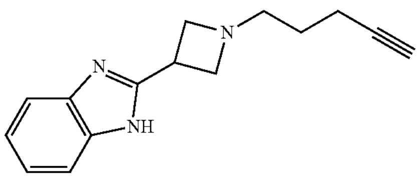 [SMILES: C#CCCCN1CC(c2nc3ccccc3[nH]2)C1] | 1H NMR (600 MHz, Chloroform-d) δ 7.55 (broad s, 2H), 7.22 (m, 2H), 3.82 (tt, J = 7.4, 4.6 Hz, 1H), 3.60 (t, J = 7.5 Hz, 2H), 3.55 (m, 2H), 2.63 (t, J = 7.1 Hz, 2H), 2.26 (td, J = 6.9, 2.6 Hz, 2H), 2.02 (m, 1H), 1.97 (t, J = 2.7 Hz, 2H) |
| RLM-266 | 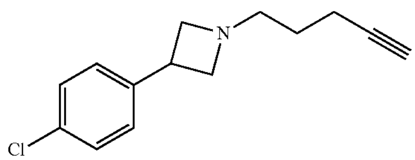 [SMILES: C#CCCCN1CC(c2ccc(Cl)cc2)C1] | 1H NMR (600 MHz, Chloroform-d) δ 7.28 (m, 4H), 3.73 (t, 2H), 3.68 (m, 1H), 3.11 (t, J = 5.3 Hz, 2H), 2.58 (qd, J = 6.6, 5.9, 2.6 Hz, 2H), 2.26 (tt, J = 7.1, 3.5 Hz, 2H), 1.60 (m, 2H), 1.27 (s, 1H) |
| RLM-275 | 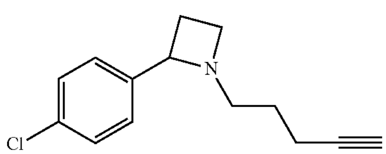 | 1H NMR (600 MHz, Chloroform-d) δ 7.35 (dd, J = 8.5, 1.7 Hz, 2H), 7.29 (m, 2H), 3.93 (t, J = 8.2 Hz, 1H), 3.43 (m, 1H), 2.83 (m, 1H), 2.62 (dtd, J = 11.8, 7.5, 1.6, Hz, 1H), 2.50 (dtd, J = 11.6, 7.5, 1.6 Hz, 1H), 2.30 (qt, J = 7.6, 1.9 Hz 1H), 2.26-2.10 (m, 2H), 2.06 (m, 1H), 1.91 (s, 1H), 1.50 (m, 2H) |
| RLM-277 | 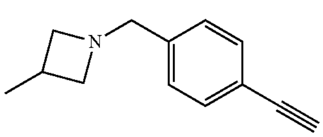 | 1H NMR (600 MHz, Chloroform-d) δ 7.47 (m, 2H), 7.33 (m, 2H), 3.80 (s, 2H), 3.72 (m, 2H), 3.09 (s, 1H), 3.06 (d, J = 7.9 Hz, 2H), 2.78 (dp, J = 14.5, 7.3 Hz, 1H), 1.21 (d, J = 6.8 Hz, 3H) |

TABLE 1-continued

| Example | Structure | ¹H-NMR |
|---|---|---|
| TH058 | 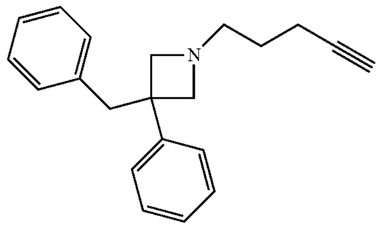 [SMILES: C#CCCCN1CC(Cc2ccccc2)(c2ccccc2)C1] | ¹H NMR (600 MHz, Chloroform-d) δ 7.21-7.05 (m, 6H), 6.75-6.65 (m, 4H), 3.66 (d, J = 5.6 Hz, 2H), 3.26 (d, J = 2.1 Hz, 2H), 3.22-3.16 (m, 2H), 2.53 (td, J = 7.3, 2.1 Hz, 2H), 1.93 (d, J = 2.5 Hz, 1H), 1.60 (td, J = 7.3, 2.2 Hz, 2H). |
| TH059 | 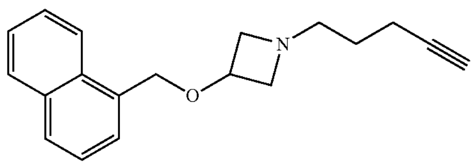 [SMILES: C#CCCCN1CC(OCc2cccc3ccccc23)C1] | ¹H NMR (600 MHz, Chloroform-d) δ 8.08 (d, J = 8.3 Hz, 1H), 7.83 (dd, J = 28.8, 7.9 Hz, 2H), 7.57-7.37 (m, 4H), 4.88 (d, J = 1.2 Hz, 2H), 4.27 (td, J = 6.0, 1.4 Hz, 1H), 3.57 (ddd, J = 8.0, 6.1, 1.6 Hz, 2H), 2.85 (ddd, J = 8.1, 6.2, 1.6 Hz, 2H), 2.50 (td, J = 7.2, 1.4 Hz, 2H), 2.18 (tdd, J = 7.1, 2.8, 1.4 Hz, 2H), 1.94-1.86 (m, 1H), 1.53 (td, J = 7.2, 1.4 Hz, 2H). |
| TH060 | 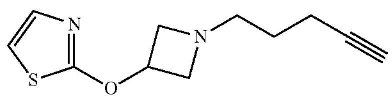 | ¹H NMR (600 MHz, Chloroform-d) δ 7.08 (dd, J = 3.9, 2.4 Hz, 1H), 6.66 (dd, J = 3.8, 2.5 Hz, 1H), 5.24 (td, J = 5.6, 2.1 Hz, 1H), 3.87-3.70 (m, 2H), 3.17 (ddt, J = 7.4, 5.0, 2.3 Hz, 2H), 2.59 (td, J = 7.2, 2.3 Hz, 2H), 2.21 (tt, J = 7.1, 2.6 Hz, 2H), 1.93 (t, J = 2.6 Hz, 1H), 1.57 (td, J = 7.2, 2.3 Hz, 2H). |
| TH061 | 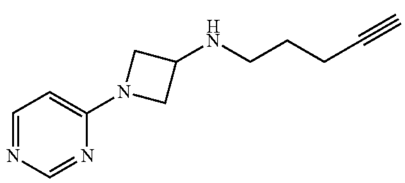 [SMILES: C#CCCCNC1CN(c2ccncn2)C1] | ¹H NMR (600 MHz, Chloroform-d) δ 8.55 (d, J = 2.9 Hz, 1H), 8.30-8.04 (m, 1H), 6.16 (dt, J = 3.6, 1.4 Hz, 1H), 4.26 (d, J = 8.4 Hz, 2H), 4.00-3.63 (m, 3H), 2.72 (td, J = 6.9, 3.4 Hz, 2H), 2.28 (ddd, J = 7.3, 5.0, 2.4 Hz, 2H), 2.08-1.88 (m, 1H), 1.70 (td, J = 6.9, 3.4 Hz, 3H). |

TABLE 1-continued

| Example | Structure | ¹H-NMR |
|---------|-----------|--------|
| TH062 | 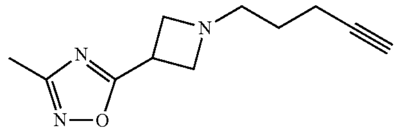 | ¹H NMR (600 MHz, Chloroform-d) δ 3.88-3.78 (m, 1H), 3.68 (ddt, J = 7.8, 6.1, 1.4 Hz, 2H), 3.36 (td, J = 7.5, 1.4 Hz, 2H), 2.55 (td, J = 7.3, 1.3 Hz, 2H), 2.36 (d, J = 1.3 Hz, 3H), 2.22-2.15 (m, 2H), 1.94-1.87 (m, 1H), 1.55 (td, J = 7.2, 1.3 Hz, 2H). |
| TH064 | 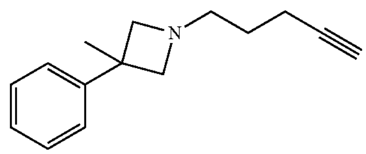 | ¹H NMR (600 MHz, Chloroform-d) δ 7.32-7.28 (m, 2H), 7.20-7.15 (m, 1H), 7.14-7.09 (m, 2H), 3.47-3.42 (m, 2H), 3.30-3.25 (m, 2H), 2.55-2.49 (m, 2H), 2.21 (td, J = 7.2, 2.6 Hz, 2H), 1.92 (t, J = 2.6 Hz, 1H), 1.61 (s, 3H), 1.61-1.55 (m, 2H). |
| TH065 | 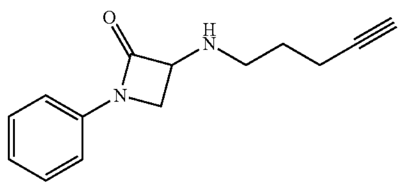 [SMILES: C#CCCCNC1CN(c2ccccc2)C1=O] | ¹H NMR (600 MHz, Chloroform-d) δ 7.37-7.30 (m, 4H), 7.09 (tt, J = 7.3, 1.4 Hz, 1H), 4.29 (dd, J = 5.3, 2.6 Hz, 1H), 3.83 (dd, J = 5.9, 5.4 Hz, 1H), 3.46 (dd, J = 5.9, 2.6 Hz, 1H), 2.97-2.79 (m, 2H), 2.29 (td, J = 7.0, 2.7 Hz, 2H), 1.95 (t, J = 2.7 Hz, 1H), 1.72 (q, J = 7.0 Hz, 2H). |
| TH066 | 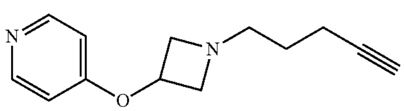 [SMILES: C#CCCCN1CC(Oc2ccncc2)C1] | ¹H NMR (600 MHz, Chloroform-d) δ 8.46-8.36 (m, 2H), 6.71-6.62 (m, 2H), 4.82 (t, J = 5.7 Hz, 1H), 3.86-3.75 (m, 2H), 3.15-3.06 (m, 2H), 2.60 (t, J = 7.2 Hz, 2H), 2.22 (td, J = 7.1, 2.7 Hz, 2H), 1.94 (t, J = 2.7 Hz, 1H), 1.58 (p, J = 7.1 Hz, 2H). |
| TH067 | 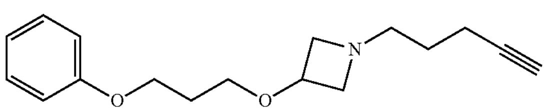 [SMILES: C#CCCCN1CC(OCCCOc2ccccc2)C1] | ¹H NMR (600 MHz, Chloroform-d) δ 7.26 (dqd, J = 9.9, 7.7 6.4, 2.8 Hz, 2H), 6.96-6.80 (m, 3H), 4.14-4.07 (m, 1H), 4.03 (dq, J = 6.1, 3.8, 2.3 Hz, 2H), 3.60 (dt, J = 6.1, 3.2 Hz, 2H), 2.84 (dd, J = 5.8, 2.6 Hz, 2H), 2.52 (dd, J = 4.8, 2.5 Hz, 2H), 2.19 (tt, J = 4.4, 2.3 Hz, 2H), 2.01 (dd, J = 7.4, 4.8 Hz, 2H), 1.95-1.87 (m, 1H), 1.60-1.48 (m, 2H). |

TABLE 1-continued

| Example | Structure | ¹H-NMR |
|---------|-----------|--------|
| TH068 | 4-NC-C₆H₄-O-azetidine-N-CH₂CH₂CH₂C≡CH | ¹H NMR (600 MHz, Chloroform-d) δ 7.60-7.42 (m, 2H), 6.91-6.65 (m, 2H), 4.79 (td, J = 5.7, 1.6 Hz, 1H), 3.79 (td, J = 7.3, 1.8 Hz, 2H), 3.10 (ddd, J = 6.9, 5.2, 2.6 Hz, 2H), 2.59 (td, J = 7.1, 1.6 Hz, 2H), 2.22 (tt, J = 7.0, 2.2 Hz, 2H), 1.94 (q, J = 2.4 Hz, 1H), 1.58 (td, J = 7.1, 1.7 Hz, 2H). |
| TH069 | 4-F-C₆H₄-azetidine-N-CH₂CH₂CH₂C≡CH | ¹H NMR (600 MHz, Chloroform-d) δ 7.27-7.18 (m, 2H), 6.98 (t, J = 8.7 Hz, 2H), 3.72 (t, J = 7.3 Hz, 2H), 3.67 (p, J = 7.4 Hz, 1H), 3.08 (t, J = 7.1 Hz, 2H), 2.56 (t, J = 7.2 Hz, 2H), 2.24 (td, J = 7.1, 2.6 Hz, 2H), 1.95 (t, J = 2.6 Hz, 1H), 1.66-1.52 (m, 2H). |
| TH070 | 3-F-C₆H₄-azetidine-N-CH₂CH₂CH₂C≡CH | ¹H NMR (600 MHz, Chloroform-d) δ 7.30-7.16 (m, 1H), 7.05-6.95 (m, 2H), 6.89 (td, J = 8.4, 2.5 Hz, 1H), 3.79-3.54 (m, 3H), 3.15-3.01 (m, 2H), 2.55 (t, J = 7.2 Hz, 2H), 2.24 (td, J = 7.2, 2.6 Hz, 2H), 1.94 (td, J = 2.6, 0.8 Hz, 1H), 1.59 (p, J = 7.2 Hz, 2H). |
| TH071 | 2-F-C₆H₄-azetidine-N-CH₂CH₂CH₂C≡CH | ¹H NMR (600 MHz, Chloroform-d) δ 7.28 (tdd, J = 7.5, 1.7, 0.8 Hz, 1H), 7.17 (dddd, J = 7.7, 7.0, 5.1, 1.8 Hz, 1H), 7.09 (td, J = 7.5, 1.3 Hz, 1H), 6.97 (ddd, J = 10.3, 8.1, 1.2 Hz, 1H), 3.91 (p, J = 7.9 Hz, 1H), 3.82-3.72 (m, 2H), 3.16-3.06 (m, 2H), 2.54 (t, J = 7.2 Hz, 2H), 2.23 (td, J = 7.1, 2.7 Hz, 2H), 1.94 (t, J = 2.7 Hz, 1H), 1.64-1.53 (m, 2H). |

TABLE 1-continued

| Example | Structure | ¹H-NMR |
|---|---|---|
| TH072 | 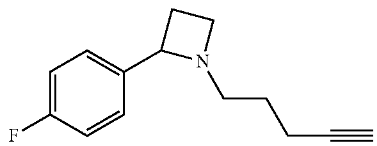 [SMILES: C#CCCCN1CCC1c1ccc(F)cc1] | ¹H NMR (600 MHz, Chloroform-d) δ 7.39-7.33 (m, 2H), 6.99 (td, J = 8.6, 1.4 Hz, 2H), 3.92 (t, J = 8.1 Hz, 1H), 3.45-3.37 (m, 1H), 2.85-2.77 (m, 1H), 2.60 (dt, J = 11.4, 7.5 Hz, 1H), 2.48 (dt, J = 11.1, 6.7 Hz, 1H), 2.30-2.24 (m, 1H), 2.23-2.09 (m, 2H), 2.01 (p, J = 9.2 Hz, 1H), 1.89 (d, J = 1.5 Hz, 1H), 1.53-1.44 (m, 2H). |
| TH073 | 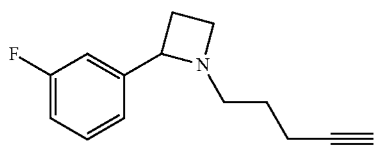 [SMILES: C#CCCCN1CCC1c1cccc(F)c1] | ¹H NMR (600 MHz, Chloroform-d) δ 7.31-7.20 (m, 1H), 7.19-7.09 (m, 2H), 6.90 (tdd, J = 8.5, 2.6, 1.0 Hz, 1H), 3.95 (t, J = 8.1 Hz, 1H), 3.42 (dddd, J = 8.3, 6.5, 2.0, 0.8 Hz, 1H), 2.83 (ddd, J = 9.6, 7.7, 6.4 Hz, 1H), 2.62 (dt, J = 11.6, 7.5 Hz, 1H), 2.48 (dt, J = 11.6, 6.7 Hz, 1H), 2.29 (dtd, J = 9.8, 7.6, 2.0 Hz, 1H), 2.26-2.19 (m, 1H), 2.19-2.12 (m, 1H), 2.01 (tt, J = 10.0, 8.4 Hz, 1H), 1.90 (t, J = 2.7 Hz, 1H), 1.51 (p, J = 7.1 Hz, 2H). |
| TH074 | 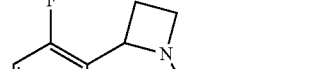 | ¹H NMR (600 MHz, Chloroform-d) δ 7.67 (tdd, J = 7.5, 1.9, 0.7 Hz, 1H), 7.21-7.16 (m, 1H), 7.13 (td, J = 7.4, 1.2 Hz, 1H), 6.95 (ddd, J = 10.3, 8.1, 1.3 Hz, 1H), 4.31 (t, J = 8.2 Hz, 1H), 3.52-3.37 (m, 1H), 2.88 (ddd, J = 9.6, 7.8, 6.6 Hz, 1H), 2.66 (dt, J = 11.7, 7.7 Hz, 1H), 2.49 (dt, J = 11.5, 6.5 Hz, 1H), 2.41-2.31 (m, 1H), 2.22 (dtd, J = 15.6, 7.1, 2.6 Hz, 2H), 2.03 (ddd, J = 9.9, 8.7, 1.5 Hz, 1H), 1.92-1.83 (m, 1H), 1.58-1.48 (m, 2H). |

Evaluation of Ring-Opening Under Biological Conditions

An exemplary azetidine compound (RLM207) was dissolved in deuterated PBS with either cysteine (1.5 mmol eq.) or glutathione (1.5 mmol eq.), and incubated at 37° C. for 24 hrs in phosphate-buffered saline and DMF (5:1). To observe if any products formed between the RLM207 and biological nucleophiles, high-resolution LC-MS/MS was used to analyze the two reactions. Samples were desalted on a STAGE-Tip $C^{18}$ column and dissolved in mobile phase A (0.1% formic acid) for LC-MS/MS analysis. While no change was observed in the cysteine sample, there was a marked difference in the glutathione reaction. Thus, at 24.46 min, there appeared a peak with an M+1 mass of 547.2336 m/z corresponding to the covalent product. MS2 fragmentation further demonstrated that RLM207 had bound to the cysteine of glutathione, thereby illustrating that azetidines are capable of ring-opening under biological conditions.

The disparity between free cysteine and glutathione indicated that azetidines cannot react with a single amino acid, but will undergo ring-opening with a tri-peptide. This result can be attributed to a possible tertiary structure forming between glutathione and RLM207 to activate the azetidine, or simply the enhanced nucleophilic nature of cysteine within glutathione. Ring-opening reactions of azetidines typically employ harsh conditions that are not amenable to biological samples, such as strong acids and organic solvents[12-15]. Our discovery was the first indication that azetidines form covalent products with a tripeptide.

Testing Azetidine Compounds for Binding to Proteins in Gel Assay

Figure 2:
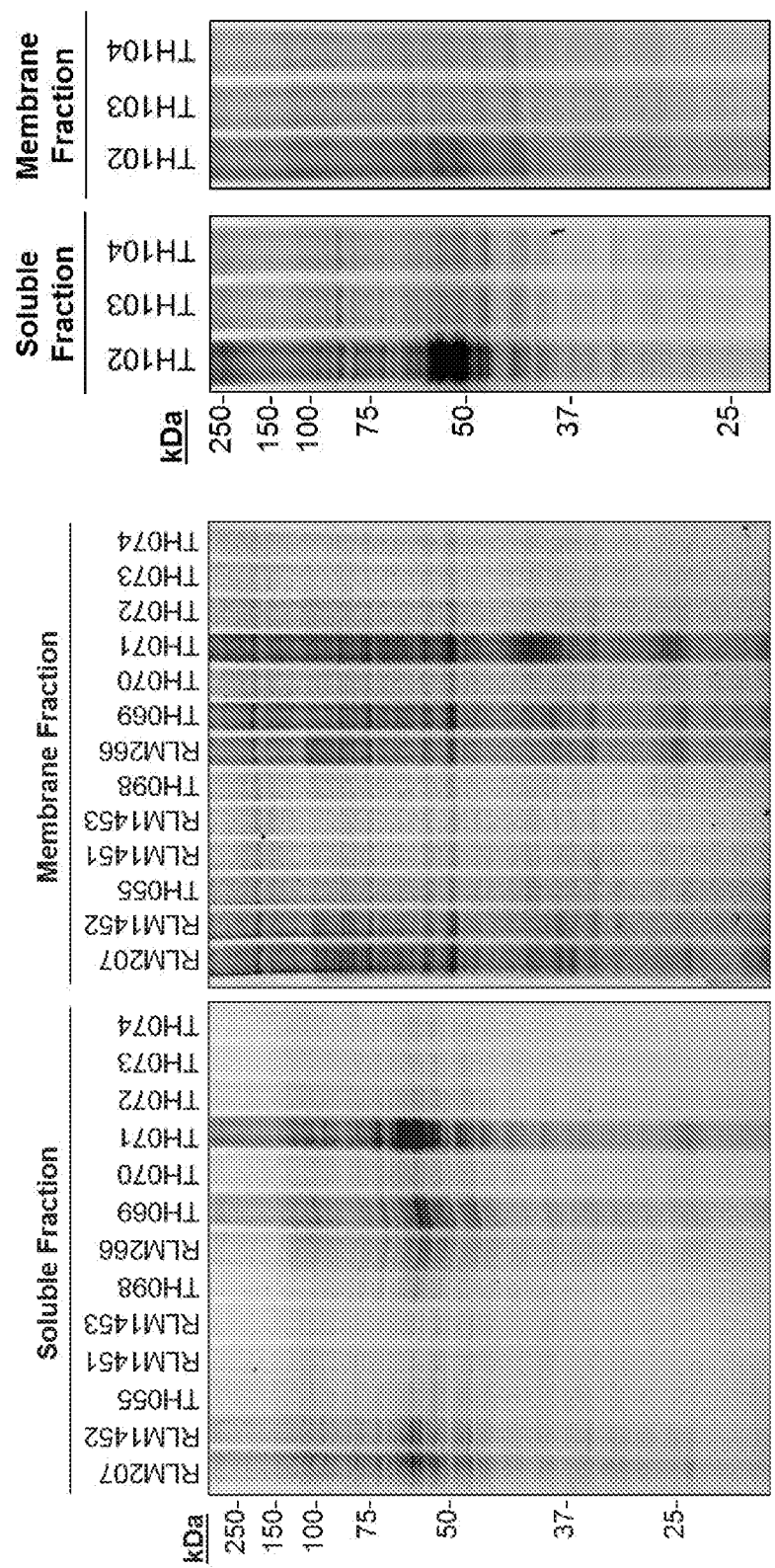
FIG. 2. Structure activity relationship studies of some azetidine compounds of the present disclosure and their reactivity. Cell lysates were incubated with the indicate azetidine compounds for 1 hr for gel experiments and 3 hrs for LC-MS/MS experiments. Rhodamine or desthiobiotin tags were appended to the probe for gel and mass spectrometry experiments, respectively, by copper-catalyzed azide-alkyne cycloaddition, i.e., CLICK chemistry.
Figure 3:
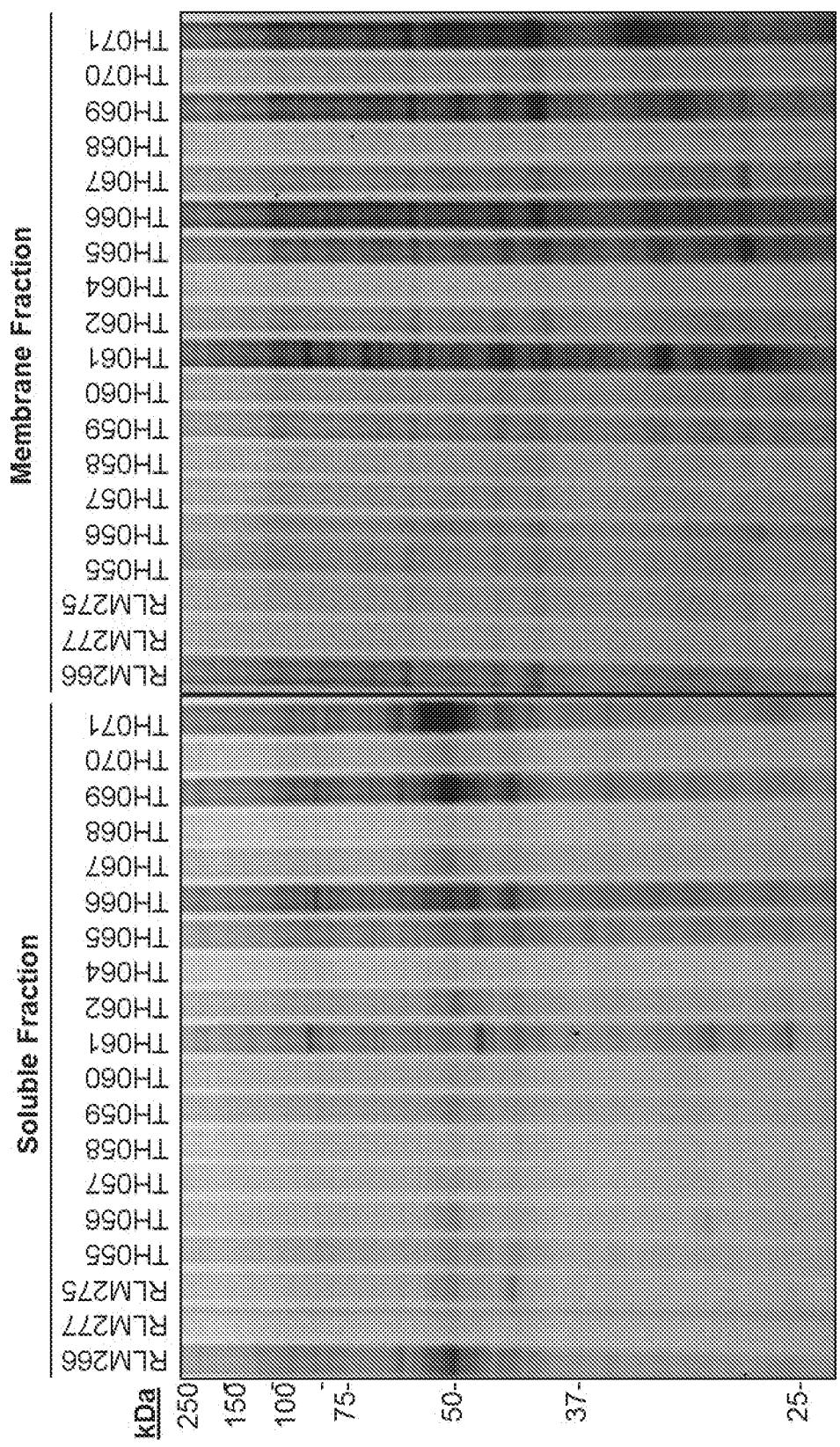
FIG. 3. Additional structure activity relationship studies of some azetidine compounds of the present disclosure and their reactivity.
Figure 4:
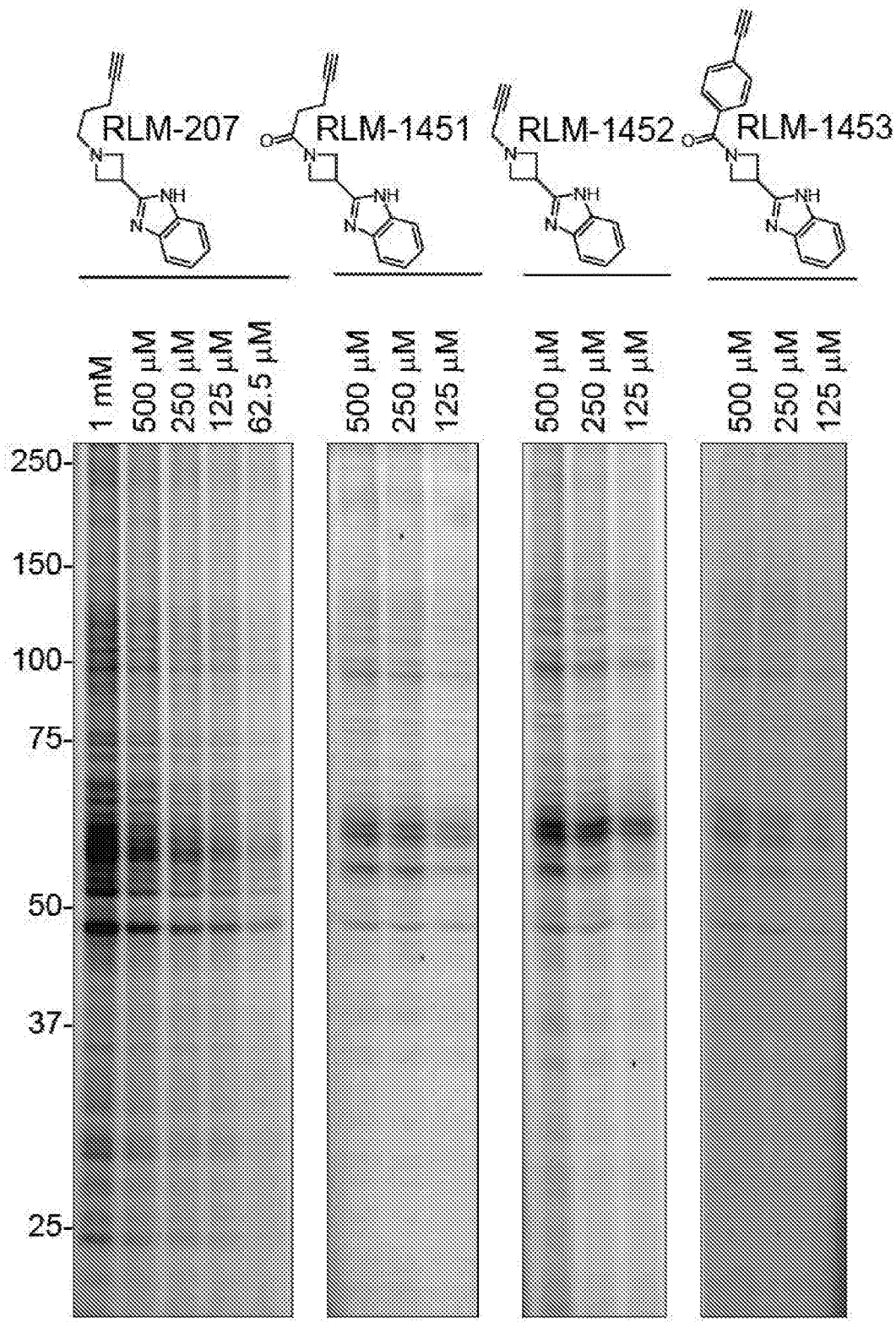
FIG. 4. Dose dependent binding of some azetidine compounds to proteins in HEK293T cell lysate.

Continuing with the benzimidazole azetidine, we appended different alkyne tags via reductive amination or HATU coupling to observe the effects of N-substituents on the ring (Scheme 1 above). Soluble and membrane HEK293T cell proteomes were treated with 25 μM of azetidine compounds for one hour before addition of rhodamine via CLICK chemistry, i.e., copper catalyzed azide-alkyne cycloaddition (CuAAC). After the proteins were resolved via SDS-PAGE, we discovered a robust and unique binding profile from the azetidine probes (FIG. 2 and FIG. 3).

Fluorophenyl compounds TH069 and TH071 were observed to be the most reactive. Moving the aryl substituent to the 2-position of the azetidine ring resulted in no improvement in azetidine reactivity, likely due to steric inhibition of biological nucleophiles for the ring-opening reaction. Because fluorine atoms are known to possess unique biological properties, we substituted the fluorophenyl substituents for a pyridine ring. Similar trends were observed suggesting that it is beneficial to install electron-withdrawing groups at the 2 and 4-positions of aromatic substituents to enhance azetidine reactivity in human proteomes. These results illustrate that azetidine compounds described herein possess inherent reactivity for use as ABPs.

N-acyl azetidines were not as reactive as their aliphatic cohorts. Decreased labeling was likely due to the delocalization of the nitrogen's lone pair of electrons, preventing the formation of the azetidinium ion for ring-opening. Additionally, the 3-carbon linker to the alkyne tag was optimal, allowing the azide to come into contact to the alkyne even when proteins aggregated in the click chemistry step. Knowing these factors, we continued to optimize the structure and improve azetidine reactivity. As we continued our analysis of azetidine substituents, the pentyne tag was preserved for optimal CuAAC labeling.

Replacement of the benzimidazole moiety in favor for a phenyl group on TH098 did not improve protein binding, but appending electron withdrawing groups enhanced the efficiency of the reaction. The comparison between chlorine and fluorine substituents on RLM266 and TH069 showed that the fluorophenyl azetidines were even more reactive. As the fluorine was moved to the meta (TH070) and ortho (TH071) positions on the ring, we discovered that the meta fluorine was the least reactive. The fluorophenyl was subsequently moved to the 2-position on the azetidine ring (M071, TH073, and TH074), where we found that we could not recover probe labeling by repositioning the fluorine atom. Moving the bulky phenyl group suggested that steric hinderance at the 2 or 3-position on the ring would prevent a nucleophile from attacking the azetidine ring, and it provided further support for our predicted mechanism. We found that TH071, a 3(O-fluorophenyl) azetidine, displayed the best reactivity for our gel studies. Because fluorine atoms often show unique properties, we tested regioisomers of 3-pyridine azetidine probes to observe if this trend was consistent when the fluorophenyls were replaced. Using our gel ABPP assay, we confirmed a general trend for incorporating electron-withdrawing groups on the azetidine compounds, thereby increasing the electrophilic nature of the azetidine ring.

Azetidine Compounds Target Redox Proteins and Lipid Kinases

Our initial attempts to enrich for azetidine-bound peptides were not optimal when we treated HEK lysates with only 25 μM of azetidine compound, illustrated by TH071. While we could easily observe protein bands by gel fluorescence, we were not saturating the proteome. Because many of the azetidine compounds are considered fragment compounds (MW<250 g/mol), they do not remain in protein binding pockets long enough to guarantee a covalent reaction.

However, once we increased the concentration of TH071 to 0.5 mM, we identified multiple azetidine-tagged proteins. Next, isotopically labeled proteins were obtained through routine procedures using labeled amino acids, and the proteins were then reacted with TH071 for 3 hrs before click chemistry with desthiobiotin azide for 2 hours. Proteins were digested by trypsin into peptides before azetidine-bound peptides were enriched via affinity chromatography. Eluted peptides were analyzed by high resolution LC-MS/MS using a top 10 data-dependent acquisition (DDA). An added mass of 631.3858 Da was used to search for azetidine modifications to amino acid residues. Peptides were quantified between samples by measuring the integration of MS1 peaks between heavy and light peptides, and were sequenced by manual verification of MS2 fragmentation spectra. By this approach, we found that many of the tagged peptides were shown to possess sulfhydration sites, specifically with GSTP1, PEBP1, GAPDH, and ribosomal subunits (FIG. 5). Sulfhydration modifications are a form of cysteine oxidation after the reaction with $H_2S$ to form a persulfide (S—SH). This post-translational modification has been shown to affect protein activity and localization.[16,17] MS2 spectra identified the location of TH071 modification at cysteine residues which form persulfides in the presence of $H_2S$, indicating that the microenvironment around these residues can permit azetidine ring-opening.

Due to the lipophilic nature of azetidines, we also tested TH071 on recombinant mammalian DGKα and enriched for four peptides that were unique to this azetidine compound. Of these sites, two are located adjacent to the active site, one within the catalytic domain, and another in the zinc finger domain. These results presented the question regarding the significance of these sites on DGKα and if they play a role in regulating this protein. DGKs attenuate the interconversion of diacylglycerol (DAG) to phosphatidic acid (PA). Both DAG and PA act as important second messengers within cells, and improper regulation of these lipids can result in neurodegenerative disease, diabetes, and T-cell anergy. DGKα is highly expressed in immune cells, and it has become an attractive target for immunotherapies. DAG is an important signaling molecule to allow T-cell activation and proliferation, and it was discovered that overactive DGKα can induce T-cell anergy. While there have been multiple efforts to repurpose drugs and elucidate the structure, our understanding of DGKα continues to fall short. Even today, we have a minimal understanding of how this protein is regulated in T-cells at the protein level. After identifying that persulfide sites were targeted by azetidines, we set out to determine if DGKα was sensitive to $H_2S$ and if persulfides formed at the azetidine-binding sites.

Azetidine Probes Enable Sulfhydration Studies of DGKα

T-cells require endogenous $H_2S$ to activate and proliferate. Cystathionine β-synthase (CBS) and Cystathionine γ-lyase (CSE) are two proteins responsible for generating $H_2S$, and previous studies have shown how knockdown of these proteins can drastically impair T-cell function. We initially tested if DGKα was affected by sulfur donors in a recombinant system. Thus, HEK293T cells expressing recombinant rat DGKα were treated with $Na_2S_4$ for 1 hr for luminescent ADP detection assay (ADP-Glo) and ABPP experiments. The activity of the rat isoform in our ADP-Glo™ assay (Promega Corporation) decreased by 40% at 10 μM 30% at 1 μM of the sulfur donor. Using TH071, we employed competitive ABPP and found that these results were recapitulated in our gel assay described above. When DGKζ was tested in a similar manner, the substrate assay showed no effect while TH071 failed to label the protein. DGKζ is also present in T-cells, and while it bears similarities to the alpha isoform in the catalytic domain, it may have a different conformation, preventing the azetidine compound from binding to the active site. These results indicate that the reactive cysteines of DGKα may lie within unique binding pockets that are not found on DGKζ.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this present disclosure has been disclosed with reference to specific embodiments, it is apparent that other embodiments and variations of this present disclosure may be devised by others skilled in the art without departing from the true spirit and scope of the present disclosure.

BIBLIOGRAPHY

References cited herein, including numbered references, are as follows:

Yang & Liu; Chem. Biochem., 2015
Hacker, et. al; Nature Chem, 2017
Cravatt, et. al.; Ann. Rev. Biochem., 2008
Yoda, et. al; Heterocycles in Natural Product Synthesis, 2011
Gaertner; J. Het., 1969
Alvi, et. al.; Bioorg. Med. Chem. Lett., 1994
Karpievitch, et. al.; Ann Appl Stat., 2010
Mei, et. al.; Int. J. of Hydrogen Energy, 2016
Mei., et. al; Tet. Lett., 2017

1. Zhang, T. Y., Chapter One—The Evolving Landscape of Heterocycles in Drugs and Drug Candidates. In *Advances in Heterocyclic Chemistry*, Scriven, E. F. V.; Ramsden, C. A., Eds. Academic. Press: 2017; Vol. 121, pp 1-12.
2. Vitaku, E.; Smith, D. T.; Njardarson, J. T., Analysis of the Structural Diversity, Substitution Patterns, and Frequency of Nitrogen Heterocycles among U.S. FDA Approved Pharmaceuticals. *Journal of Medicinal Chemistry* 2014, 57 (24), 10257-10274.
3. Palkowitz, M. D.; Tan, B.; Hu, H.; Roth, K.; Bauer, R. A., Synthesis of Diverse N-Acryloyl Azetidines and Evaluation of Their Enhanced Thiol Reactivities. *Organic Letters* 2017, 19 (9), 2270-2273.
4. Kato, N.; Comer, E.; Sakata-Kato, T.; Sharma, A.; Sharma, M.; Maetani, M.; Bastien, J.; Brancucci, N. M.; Bittker, J. A.; Corey, V.; Clarke, D.; Derbyshire, E. R.; Dornan, G. L.; Duffy, S.; Eckley, S.; Itoe, M. A.; Koolen, K. M. J.; Lewis, T. A.; Lui, P. S.; Lukens, A. K.; Lund, E.; March, S.; Meibalan, E.; Meier, B. C.; McPhail, J. A.; Mitasev, B.; Moss, E. L.; Says, M; Van Gessel, Y.; Wawer, M. J.; Yoshinaga, T.; Zeeman, A.-M.; Avery, V. M.; Bhatia, S. N.; Burke, J. E.; Catteruccia, F.; Clardy, J. C.; Clemons, P. A.; Dechering, K. J.; Duvall, J. R.; Foley, M. A.; Gusovsky, F.; Kocken, C. H. M.; Marti, M.; Morningstar, M. L.; Munoz, B.; Neafsey, D. E.; Sharma, A.; Winzeler, E. A.; Wirth, D. F.; Scherer, C. A.; Schreiber, S. L., Diversity-oriented synthesis yields novel multistage antimalarial inhibitors. *Nature* 2016, 538 (7625), 344-349.
5. Maetani, M.; Zoller, J.; Melillo, B.; Verho, O.; Kato, N.; Pu, J.; Corner, E.; Schreiber, S. L., Synthesis of a Bicyclic Azetidine with In Vivo Antimalarial Activity Enabled by Stereospecific, Directed C(sp3)-H Arylation. *Journal of the American Chemical Society* 2017, 139 (32), 11300-11306.
6. Oizumi, K.; Nishino, H.; Koike, H.; Sada, T.; Miyamoto, M.; Kimura, T., Antihypertensive Effects of CS-905, a Novel Dihydropyridine $Ca^{2+}$ Channel Blocker. *The Japanese Journal of Pharmacology* 1989, 51 (1), 57-64.
7. Watanabe, M.; Hirano, T.; Okamoto, S.; Shiraishi, S.; Tomiguchi, S.; Uchino, M., Azelnidipine, a long-acting calcium channel blocker, could control hypertension without decreasing cerebral blood flow in post-ischemic stroke patients. A 123I-IMP SPECT follow-up study. *Hypertension Research* 2009, 33, 43.
8. Cravat, B. F.; Wright, A. T.; Kozarich, J. W., Activity-Based Protein Profiling: From Enzyme Chemistry to Proteomic Chemistry. *Annual Review of Biochemistry* 2008, 77 (1), 383-414.
9. Lanning, B. R.; Whitby, L. R.; Dix, M. M.; Douhan, J.; Gilbert, A. M.; Hett, E. C.; Johnson, F. O.; Joslyn, C.; Kath, J. C.; Niessen, S.; Roberts, L. R.; Schnute, M. E.; Wang, C.; Hulce, J. J.; Wei, B.; Whiteley, L. O.; Hayward, M. M.; Cravatt, B. F., A road map to evaluate the proteome-wide selectivity of covalent kinase inhibitors. *Nature chemical biology* 2014, 10 (9), 760-767.
10. Liu, Y.; Patricelli, M. P.; Cravatt, B. F., Activity-based protein profiling: The serine hydrolases. *Proceedings of the National Academy of Sciences* 1999, 96 (26), 14694.
11. Bera, M.; Pratihar, S.; Roy, S., Ag(I)-Catalyzed Regioselective Ring-Opening of N-Tosylaziridine and N-Tosylazetidine with S-, O-, and N-Nucleophiles and Tethered Dinucleophiles. *The Journal of Organic Chemistry* 2011, 76 (5), 1475-1478.
12. Dwivedi, S. K.; Gandhi, S.; Rastogi, N.; Singh, V. K.; Lewis acid catalyzed regioselective ring opening of azetidines with alcohols and thiols. *Tetrahedron Letters* 2007, 48 (31), 5375-5377.
13. Ghorai, M. K.; Kumar, A.; Tiwari, D. P., BF3.OEt2-Mediated Highly Regioselective SN2-Type Ring-Opening of N-Activated Aziridines and N-Activated Azetidines by Tetraalkylammonium Halides. *The Journal of Organic Chemistry* 2010, 75 (1), 137-151.
14. Ghorai, M. K.; Shukla, D.; Bhattacharyya, A., Syntheses of Chiral β- and γ-Amino Ethers, Morpholines, and Their Homologues via Nucleophilic Ring-Opening of Chiral Activated Aziridines and Azetidines. *The Journal of Organic Chemistry* 2012, 77 (8), 3740-3753.

15. Wang, Z.; Sheong, F. K.; Sung, H. H. Y.; Williams, I. D.; Lin, Z.; Sun, J., Catalytic Enantioselective Intermolecular Desymmetrization of Azetidines. *Journal of the American Chemical Society* 2015, 137 (18), 5895-5898.

16. Miller, T. W.; Wang, E. A.; Gould, S.; Stein, E. V.; Kaur, S.; Lim, L.; Amarnath, S.; Fowler, D. H.; Roberts, D. D., Hydrogen Sulfide Is an Endogenous Potentiator of T Cell Activation. *Journal of Biological Chemistry* 2012, 287 (6), 4211-4221.

17. Yang, R.; Qu, C.; Zhou, Y.; Konkel, J. E.; Shi, S.; Liu, Y.; Chen, C.; Liu, S.; Liu, D.; Chen, Y.; Zandi, E.; Chen, W.; Zhou, Y.; Shi, S., Hydrogen Sulfide Promotes Tet1- and Tet2-Mediated Foxp3 Demethylation to Drive Regulatory T Cell Differentiation and Maintain Immune Homeostasis. *Immunity* 2015, 43 (2), 251-263.

We claim:

1. An azetidine compound of Formula I or a pharmaceutically acceptable salt thereof:

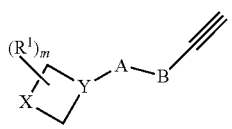

(I)

wherein
A is —NH;
X is NR$^4$ and Y is CH;
B is a bond, C$_1$-C$_6$-alkylene, or —(C$_1$-C$_6$-alkylene)(C$_6$-C$_{12}$-arylene);
R$^1$ is selected from the group consisting of H and C$_6$-C$_{12}$-aryl;
R$^4$ is selected from the group consisting of C$_6$-C$_{12}$-aryl, 5- to 12-membered heteroaryl (wherein one or more members is selected from N, O, and S), 5- to 12-membered —O-(heteroaryl) (wherein one or more members is selected from N, O, and S), and 4- to 12-membered heterocycle (wherein one or more members is selected from N, O, and S);
m is 0, 1, 2, 3, or 4; and
any aryl, heterocycle, or heteroaryl is optionally substituted with one to four substituents selected from the group consisting of halogen, hydroxy, cyano, acyl, alkyl, alkenyl, alkynyl, cycloalkyl, heterocyclo, aryl, alkoxy, amino, amide, thiol, oxo, nitro, and carboxy.

2. The compound or pharmaceutically acceptable salt according to claim 1, wherein R$^4$ is C$_6$-C$_{12}$-aryl or 5- to 12-membered heteroaryl (wherein one or more members is selected from N, O, and S).

3. An azetidine compound of Formula I or a pharmaceutically acceptable salt thereof,

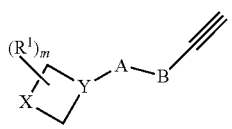

(I)

wherein
A is —CH$_2$—;
X is CR$^2$R$^3$;
Y is N;
B is —CH$_2$CH$_2$—;
R$^1$ is selected from the group consisting of H and C$_6$-C$_{12}$-aryl;
R$^2$ is H;
R$^3$ is selected from the group consisting of —(C$_1$-C$_6$-alkyl)(C$_6$-C$_{12}$-aryl), C$_6$-C$_{12}$-aryl, —O—(C$_6$-C$_{12}$-aryl); 5- to 12-membered heteroaryl except triazole and diazole (wherein one or more members is selected from N, O, and S), and 5-to 12-membered —O-(heteroaryl) (wherein one or more members is selected from N, O, and S);
m is 0, 1, 2, 3, or 4; and
any aryl, or heteroaryl is optionally substituted with one to four substituents selected from the group consisting of halogen, hydroxy, cyano, acyl, alkyl, alkenyl, alkynyl, cycloalkyl, heterocyclo, aryl, alkoxy, amino, amide, thiol, nitro, and carboxy.

4. A compound or pharmaceutically acceptable salt thereof, wherein the compound is selected from the following table:

| Example | Structure |
| --- | --- |
| TH055 | 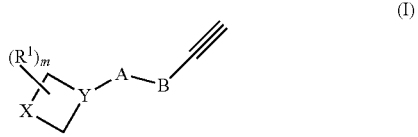 |
| TH056 | 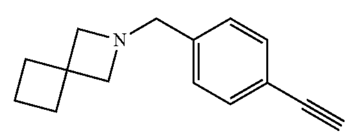 [SMILES: C#Cc1ccc(CN2CC3(CCC3)C2)cc1] |
| TH057 | 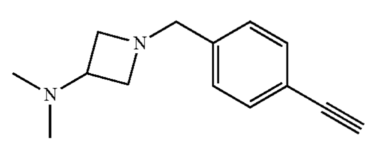 [SMILES: C#Cc1ccc(CN2CC(N(C)C)C2)cc1] |

| Example | Structure |
|---|---|
| RLM-1451 | 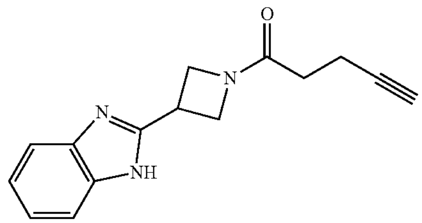 [SMILES: C#CCCC(=O)N1CC(c2nc3ccccc3[nH]2)C1] |
| RLM-1452 | 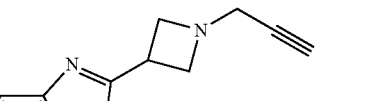 |
| RLM-1453 | 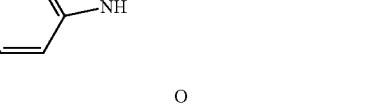 |
| RLM-207 | 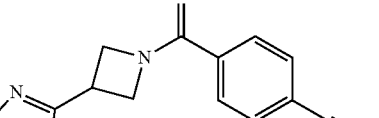 |
| RLM-266 | 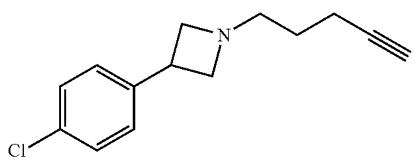 [SMILES: C#CCCCN1CC(c2ccc(Cl)cc2)C1] |
| RLM-275 | 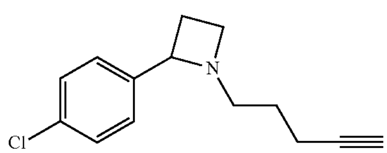 [SMILES: C#CCCCN1CCC1c1ccc(Cl)cc1] |
| RLM-277 | 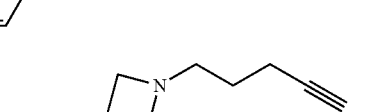 |
| TH058 | 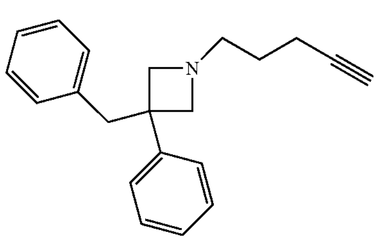 [SMILES: C#CCCCN1CC(Cc2ccccc2)(c2ccccc2)C1] |

-continued

| Example | Structure |
|---|---|
| TH059 | 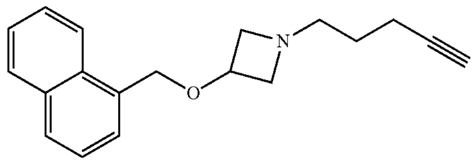 [SMILES: C#CCCCN1CC(OCc2cccc3ccccc23)C1] |
| TH060 | 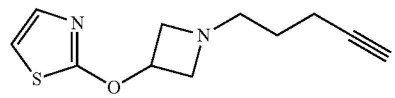 |
| TH061 | 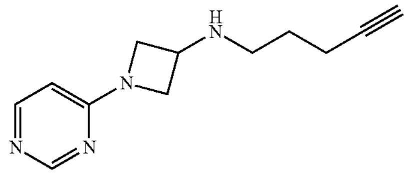 [SMILES: C#CCCCNC1CN(c2ccncn2)C1] |
| TH062 | 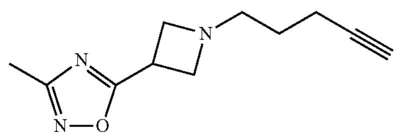 |
| TH064 | 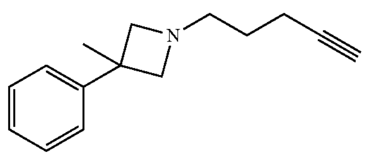 [SMILES: C#CCCCN1CC(C)(c2ccccc2)C1] |
| TH065 | 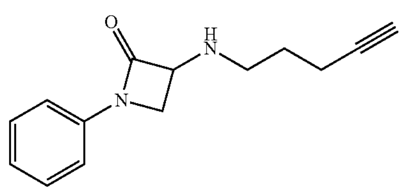 [SMILES: C#CCCCNC1CN(c2ccccc2)C1=O] |
| TH066 | 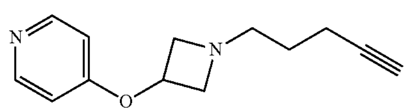 [SMILES: C#CCCCN1CC(Oc2ccncc2)C1] |
| TH067 | 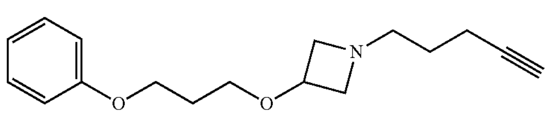 [SMILES: C#CCCCN1CC(OCCCOc2ccccc2)C1] |
| TH068 | 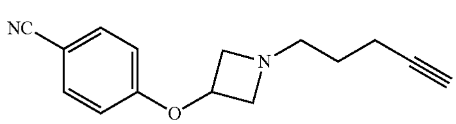 [SMILES: C#CCCCN1CC(Oc2ccc(C#N)cc2)C1] |
| TH069 | 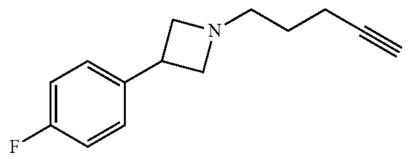 [SMILES: C#CCCCN1CC(c2ccc(F)cc2)C1] |

-continued
| Example | Structure |
|---|---|
| TH070 | 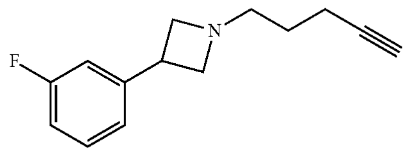 [SMILES: C#CCCCN1CC(c2cccc(F)c2)C1] |
| TH071 | 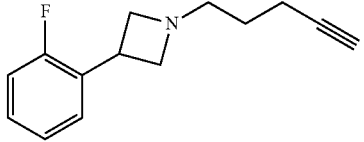 [SMILES: C#CCCCN1CC(c2ccccc2F)C1] |
| TH072 | 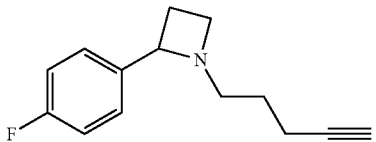 |
| TH073 | 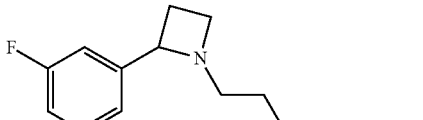 and |
| TH074 | 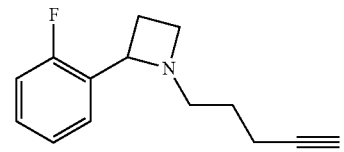 [SMILES: C#CCCCN1CCC1c1ccccc1F] . |
5. A compound or pharmaceutically acceptable salt thereof, wherein the compound is selected from the following table:
| | |
|---|---|
| RLM-1451 | 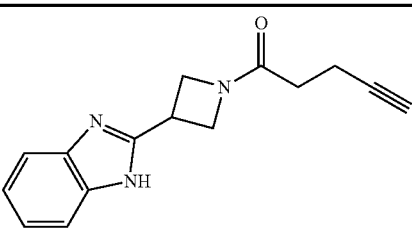 |
| RLM-1452 | 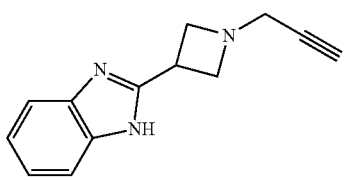 [SMILES: C#CCN1CC(c2nc3ccccc3[nH]2)C1] |
| RLM-1453 | 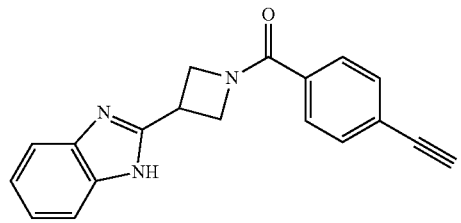 and |
| RLM-207 | 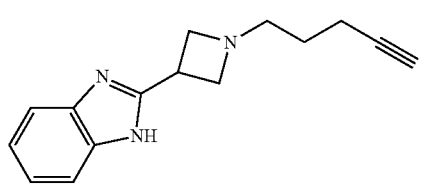 [SMILES: C#CCCCN1CC(c2nc3ccccc3[nH]2)C1] . |
* * * * *